United States Patent
Richards et al.

(10) Patent No.: US 6,208,903 B1
(45) Date of Patent: *Mar. 27, 2001

(54) MICROWAVE APPLICATOR

(75) Inventors: William F. Richards, Tuscon, AZ (US); Peter LeVay, Santa Barbara, CA (US)

(73) Assignee: Medical Contouring Corporation, Henderson, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/107,908

(22) Filed: Jun. 23, 1998

Related U.S. Application Data

(63) Continuation-in-part of application No. 08/480,620, filed on Jun. 7, 1995, now Pat. No. 5,769,879.

(51) Int. Cl.$^7$ ..................................................... A61N 5/02
(52) U.S. Cl. ........................ 607/101; 607/154; 607/156
(58) Field of Search ................................. 607/100–102, 607/154–156; 218/746–748

(56) References Cited

U.S. PATENT DOCUMENTS

| | | | |
|---|---|---|---|
| 2,283,285 | 5/1942 | Pohlman | 128/24 |
| 3,028,857 | 4/1962 | Parker | 128/24.1 |
| 3,117,571 | 1/1964 | Fry et al. | 128/24 |
| 3,237,623 | 3/1966 | Gordon | 128/24 |

(List continued on next page.)

FOREIGN PATENT DOCUMENTS

| | | |
|---|---|---|
| 2508494 | 9/1976 | (DE) . |
| 2648908 | 5/1978 | (DE) . |
| 3048682 | 9/1981 | (DE) . |

(List continued on next page.)

OTHER PUBLICATIONS

"Tumor Eradiation of RadioFrequency Therapy, Response in 21 Patients", H.H. LeVeen et al., JAMA, vol. 235, No. 20, pp. 2198–2200.

"Equipment for Local Hyperthermia Therapy of Cancer", C.F. Babbs et al., Medical Instrumentation, vol. 16, No. 5, Sep.–Oct., 1982, pp. 245–248.

(List continued on next page.)

*Primary Examiner*—Lee Cohen
(74) *Attorney, Agent, or Firm*—Christie, Parker & Hale, LLP

(57) ABSTRACT

An apparatus and method for non-invasive removal of target tissues is disclosed. The apparatus includes a microwave applicator antenna element array for introducing a plurality of cylindrical, quasi-transverse electromagnetic surface waves adjacent the target tissue. The applicator is used for reducing fatty tissue within a subcutaneous fatty layer by taking into account the differing dielectric constants of the adjacent skin and muscle layers. A cooling bolus, made of water equivalent ceramic material, actively maintains skin surface temperature below a level at which cell damage or discomfort would occur. A control system for the applicator comprises a software driven digital computer including a program for choosing antenna array excitations. The control system further includes a phase shifting circuit including a compensating network for reducing the variation in insertion loss with phase shift. A monopole-like microstrip antenna element having a plurality of shorting pins is also disclosed for adjusting the resonant frequency and input impedance of the antenna elements. In operation, the fatty cells can be reduced through necrosis or apoptosis through the application of short pulse, high temperature doses of heat using the principle of the exponential time-temperature isoeffect relationship for tissue. In another embodiment of the present invention, the fatty tissue may be infiltrated with substances by transcutaneous injection before, during or after treatment to enhance the effectiveness of the microwave applicator.

15 Claims, 18 Drawing Sheets

U.S. PATENT DOCUMENTS

| | | | |
|---|---|---|---|
| 3,499,436 | 3/1970 | Balamuth | 128/24 |
| 3,499,437 | 3/1970 | Balamuth | 128/24 |
| 3,561,430 | 2/1971 | Filler, Jr. et al. | 128/2.05 |
| 3,577,981 | 5/1971 | Kuris | 128/2 R |
| 3,589,363 | 6/1971 | Banko et al. | 128/276 |
| 3,735,755 | 5/1973 | Eggleton et al. | 128/24 A |
| 3,828,769 | 8/1974 | Mettler | 128/24 A |
| 3,958,559 | 5/1976 | Glenn et al. | 128/2 V |
| 4,140,130 | 2/1979 | Storm, III | 128/404 |
| 4,228,809 | 10/1980 | Paglione | 128/804 |
| 4,282,880 | 8/1981 | Gardineer et al. | 128/660 |
| 4,311,154 | 1/1982 | Sterzer et al. | 128/804 |
| 4,315,514 | 2/1982 | Drewes et al. | 128/653 |
| 4,324,250 | 4/1982 | Braun et al. | 128/395 |
| 4,343,301 | 8/1982 | Indech | 128/24 A |
| 4,368,410 | 1/1983 | Hance et al. | 318/116 |
| 4,374,516 | 2/1983 | Harrison | 128/1.3 |
| 4,381,009 | 4/1983 | Del Bon | 128/399 |
| 4,391,281 | 7/1983 | Green | 128/660 |
| 4,397,313 | 8/1983 | Vaguine | 128/399 |
| 4,397,314 | 8/1983 | Vaguine | 128/399 |
| 4,441,486 | 4/1984 | Pounds | 128/24 A |
| 4,527,550 | 7/1985 | Ruggera et al. | 128/1.5 |
| 4,586,512 | 5/1986 | Do-huu et al. | 128/660 |
| 4,589,422 | 5/1986 | James et al. | 128/804 |
| 4,589,424 | 5/1986 | Vaguine | 128/804 |
| 4,597,379 | 7/1986 | Kihn et al. | 128/1 R |
| 4,601,296 | 7/1986 | Yerushalmi | 128/804 |
| 4,622,972 | 11/1986 | Giebeler, Jr. | 128/399 |
| 4,638,436 | 1/1987 | Badger et al. | 364/414 |
| 4,646,756 | 3/1987 | Watmough et al. | 128/804 |
| 4,658,828 | 4/1987 | Dory | 128/660 |
| 4,658,836 | 4/1987 | Turner | 128/804 |
| 4,662,368 | 5/1987 | Hussein et al. | 128/303.1 |
| 4,674,481 | 6/1987 | Boddie, Jr. et al. | 128/1.3 |
| 4,718,429 | 1/1988 | Smidt | 128/400 |
| 4,757,820 | 7/1988 | Itoh | 128/660 |
| 4,798,215 | 1/1989 | Turner | 128/804 |
| 5,101,836 | 4/1992 | Lee | 128/804 |
| 5,143,063 | 9/1992 | Fellner | 128/399 |
| 5,295,955 | 3/1994 | Rosen et al. | 604/22 |
| 5,503,150 | 4/1996 | Evans | 128/653.1 |
| 5,507,790 | 4/1996 | Weiss | 607/100 |
| 5,540,737 | 7/1996 | Fenn | 607/101 |
| 5,769,879 * | 6/1998 | Richards et al. | 607/101 |

FOREIGN PATENT DOCUMENTS

| | | |
|---|---|---|
| 3320990 | 12/1984 | (DE) . |
| 3431314 | 3/1986 | (DE) . |
| 820814 | 9/1959 | (GB) . |

OTHER PUBLICATIONS

Ultrasonics, Theory and Application, G. L. Gooberman, Hart Publishing Co., New York (1968), section 2.6, pp. 41–44.

"Deep Local Hyperthermia For Cancer Therapy: External Electromagnetic and Ultrasound Techniques", A. Y. Cheung and A. Neyzari, Cancer Research, vol. 44, Oct. 1984, pp. 4736–4744.

R. Wayne Fritzsche, "With FDA Approval and Reimbursement in Place, Hyperthermia is Fourth Major Anticancer Weapon," *The Medical Business Journal*, Mar. 1986, pp. 80–81, 103.

A. Yerushalmi et al., "Local Microwave Hyperthermia in the Treatment of Carcinoma of the Prostate," *Oncology*, vol. 43, 1986, pp. 299–305.

"Interim Report on Results of Treatments with the HTM–3000," HRI Inc., pp. 1–30.

*Bailey's Textbook of Microscopic Anatomy*, Douglas E. Kelly et al., Williams & Wilkins, 1984, p. 473.

*Harrison's Principles of Internal Medicine*, Robert G. Petersdorf et al. editors, McGraw–Hill Book Company, 1983, pp. 570, 571, 1567.

*Synopsis of Pathology*, W. A. D. Anderson et al., The C. V. Mosby Company, 1972, p. 333.

De Wagter, C., "Computer Simulation for Local Temperature Control During Microwave–Induced Hyperthermia," *Journal Microwave Power and Electromagnetic Energy*, 1985, vol. 20, pp. 31–42.

* cited by examiner

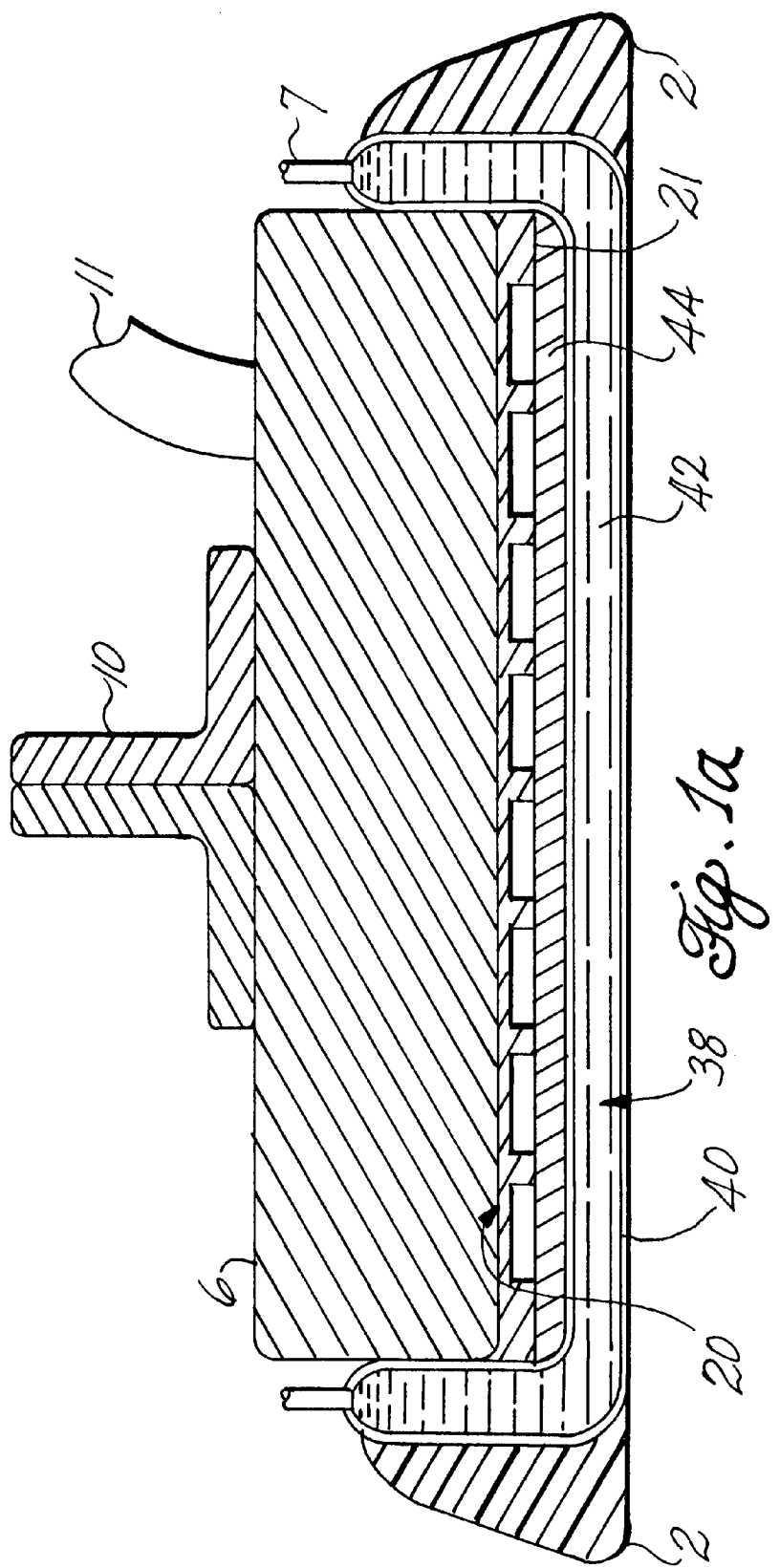

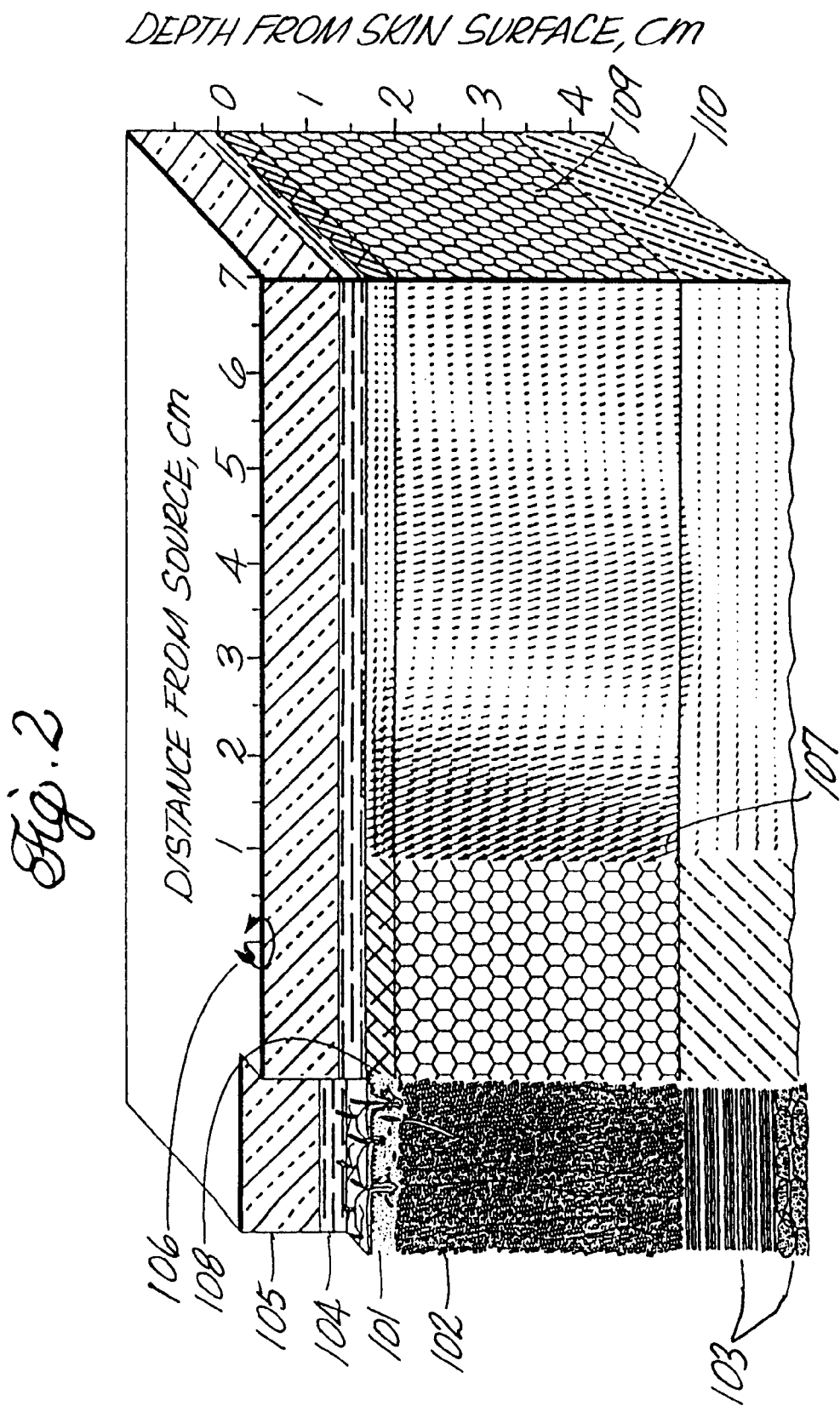

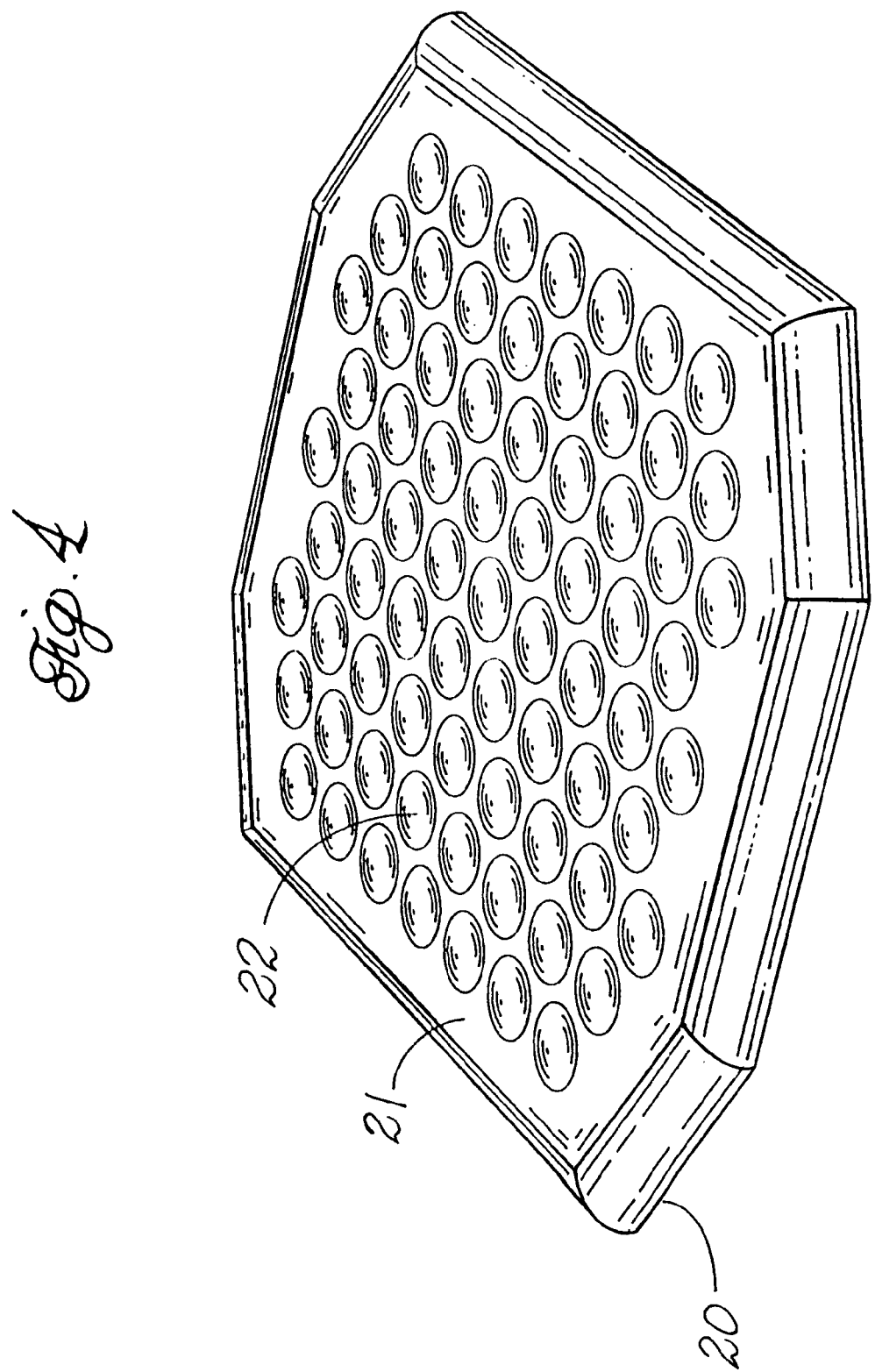

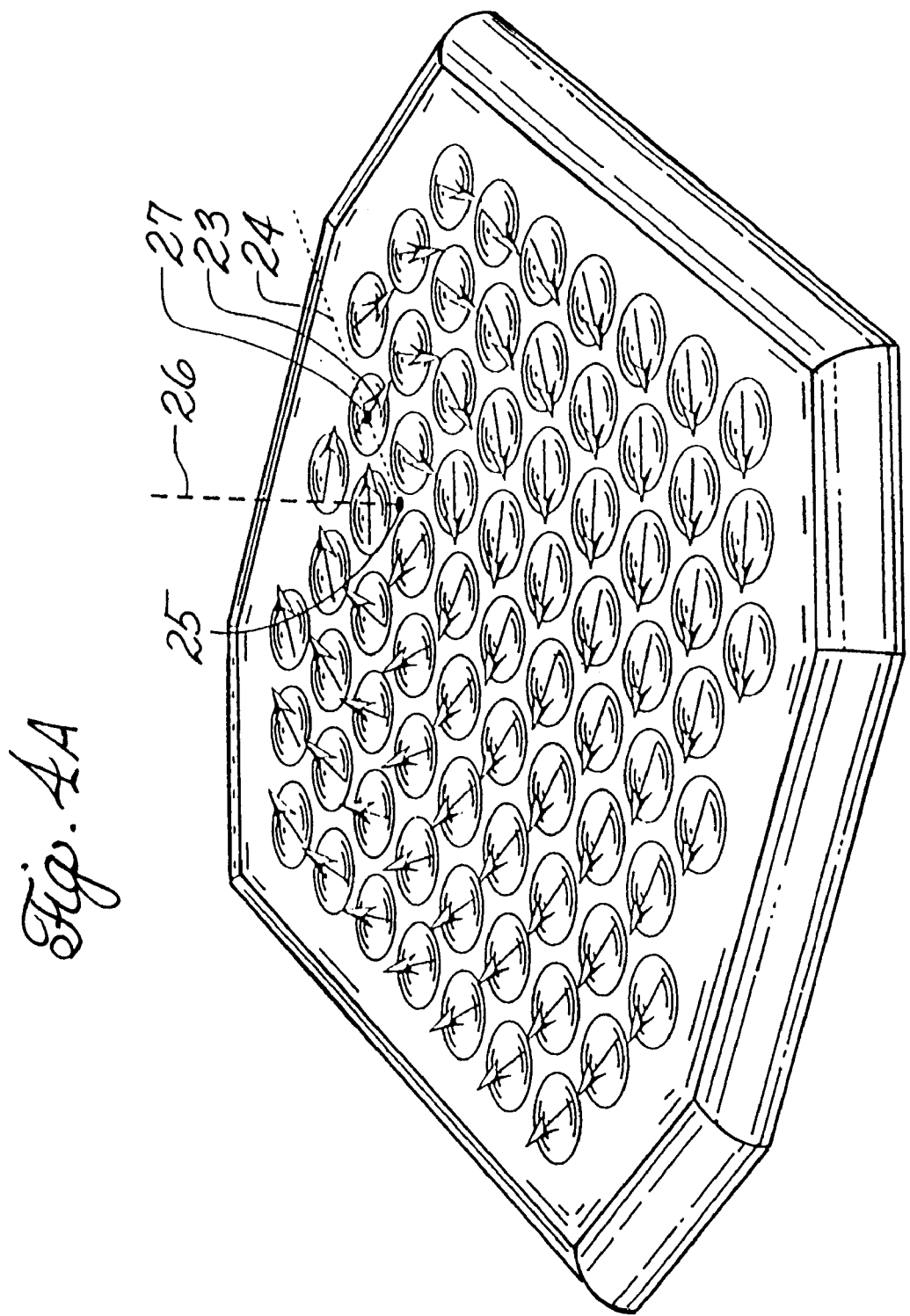

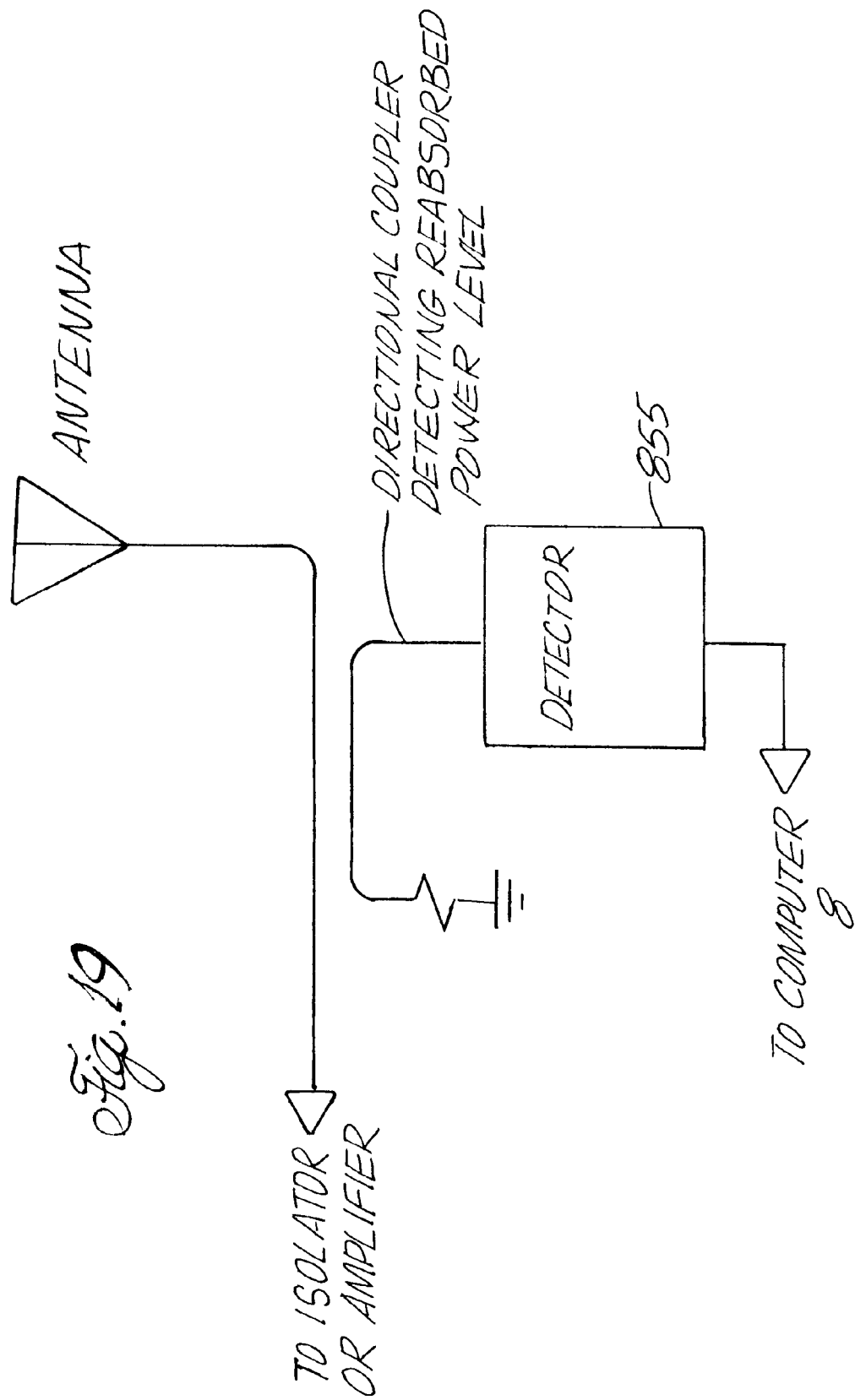

MICROWAVE APPLICATOR

CROSS REFERENCE TO RELATED APPLICATION

This application is a continuation in part of application Ser. No. 08/480,620 filed Jun. 7, 1995, now U.S. Pat. No. 5,769,879, the contents of which are hereby incorporated by reference.

FIELD OF THE INVENTION

This invention relates to a microwave applicator and the operation of that applicator to achieve hyperthermia and, more particularly, to the employment of a microwave antenna array for use in, for example, thermally induced lipoatrophy.

BACKGROUND

Hyperthermia involves the heating of living tissues for therapeutic purposes, such as for increasing blood flow to a particular part of the body. Hyperthermia has been used as a method of treating tumors by means of raising the temperature of the tumor locally, or in the region surrounding the tumor. Hyperthermia can also be effective in reducing adipose tissue through fatty cell necrosis or apoptosis.

Electromedical methods and apparatus for removing target tissue have been disclosed in conjunction with various therapeutic procedures, some of which are non-invasive. For example, U.S. Pat. No. 4,527,550 to Ruggera et al. discloses a radio-frequency diathermy apparatus, including means for localizing the heat focus for eliminating tumor cells. U.S. Pat. No. 4,397,313 to Vaguine discloses a microwave hyperthermia apparatus, including a means for focusing electromagnetic energy at a particular region of the body. U.S. Pat. No. 3,958,559 to Glenn et al. discloses an ultrasonic transducer for focusing ultrasonic waves for non-invasive treatment of internal structures, for example, tumors, within the body.

Although these systems are useful for non-invasive treatment of target tissues, none are specifically directed to the more general application of removing either tumor cells in deeper tissue layers or fat cells within a largely intact subcutaneous fat layer. In fact, each of these systems recognizes the inherent differences between fatty tissue and tumor tissue and teaches the need for avoiding damage to adipose and other normal tissues adjacent to the tumor. Vaguine and Glenn, for example, point to the differing heat tolerance of tumor cells in the context of preserving fatty and other cells adjacent the target tumor cells, not reducing them. Furthermore, the device disclosed by Vaguine uses an element field polarization more appropriate for treating deep tissues below the fat layer, rather than for treating the fat layer itself.

Accordingly, those skilled in the art would desire a generally applicable substantially non-invasive microwave applicator that could be used to induce hyperthermia in living tissue for therapeutic purposes such as either tumor removal or fatty cell necrosis.

SUMMARY

There is, therefore, provided in practice of the present invention a general purpose microwave applicator for reducing or eliminating target tissue. The applicator comprises an antenna element array, a control system and a bolus. The antenna elements generate an electromagnetic surface wave. The control system adjusts the amplitude and phase of the antenna array elements for preferentially heating target tissue. The bolus conditions the microwaves and cools the skin surface upon application of the microwaves.

In a presently preferred embodiment, the microwave applicator is used to remove adipose tissue through hyperthermia-induced fatty cell necrosis or apoptosis. In operation, the applicator generates a cylindrical, converging, quasi-transverse electromagnetic surface wave within the fat layer as a function of the differing dielectric and conductivity characteristics of the skin layer and muscle layers surrounding the fat layer. By launching a wave trapped between these layers from substantially all directions surrounding an intended focus, a converging cylindrical wave is produced which induces a column of high power density along a focal line within the fat extending from the skin-fat interface to the muscle-fat interface. The amplitude and phase for the individual antenna elements on the microwave applicator can be adjusted to move the focal line within a target fat region. Simultaneously with application, the bolus actively cools the skin surface to prevent skin burns and acute pain. As a given fat region is treated, the applicator is moved and applied over adjacent regions until the desired fat reduction is achieved.

The control system includes a computer-implemented software program for choosing antenna array excitations, and a novel phase shifting circuit. In one embodiment, the system incorporates a relatively simple and efficient method of focusing in which the amplitudes of all of the antenna input voltages are held constant and the phase is adjusted to obtain constructive interference at the projected focus. In another embodiment, the system enables adjustment of not only the focal position projected on to the bolus of the applicator but also the depth. This method involves selecting the three dimensional coordinate of the focal point, fixing the power level at that point, and reducing as much as possible the power level everywhere else.

The novel phase shifting circuit includes a two-way power divider and unidirectional amplifier for channeling power in a single direction to multiple ports, and a compensating network for reducing variation in amplitude with phase shift. An advantage of the novel phase shifter is that it replaces the typically more expensive and larger circulators used in conventional phase shifters. The novel phase shifter also has a gain generally larger than unity (instead of a positive insertion loss), and reduced output amplitude variation versus phase.

The antenna array is preferably formed of a plurality of monopole-like antenna elements. Each element includes a ground plane, a top patch insulated by a physical gap from the ground plane, a center pin connected to the top patch for feeding the antenna element, and a plurality of short circuiting pins placed symmetrically about the center pin. The shorting pins enable adjustment of the resonant frequency and input impedance of the antenna element, thereby providing additional control.

The antenna elements are preferably coupled to a novel antenna protection circuit. The antenna protection circuit includes a PIN diode, a PIN diode biasing circuit, and a detector, coupled to a PIN diode biasing circuit, for detecting power reabsorbed by the antenna element and comparing the detected power to a threshold. In operation, the detector causes the biasing circuit to bias the PIN diode as a function of the detected power such that the antenna element appears as a continuous and nonperturbing ground plane when the detected power exceeds the threshold.

The bolus preferably includes a water equivalent ceramic body and liquid-carrying channels disposed within the body.

The ceramic is preferably chosen so the leaky wave pole associated with the bolus and tissue model matches the complex wave number of fat. The bolus further includes a lossy wedge encompassing the outer periphery of the applicator for absorbing power incident on the edge of the array and reducing reflections that can result in undesired hotspots.

At least two novel methods according to the present invention are also disclosed to reduce fat. The first involves the well-controlled noninvasive induction of lethal thermal damage to fat cells over defined volumes and with relatively short-duration periods of heating using the principle of the exponential time-temperature isoeffect relationship for tissue. The second involves the well-controlled noninvasive induction of heat at levels to induce apoptosis within fat cells using either the principle of the exponential time-temperature isoeffect relationship for tissue, or using conventional hyperthermia. In operation, the control system selects the amplitude and phase of the antenna element excitation voltages for a given set of sequential foci, determines the power density at each focus, sets the heating pulse duration at each focus, and sequences the foci to obtain a substantially uniform thermal dose within the targeted fat while minimizing the maximum thermal dose in the non-target tissues.

In another embodiment of the present invention, the fatty tissue may be infiltrated with substances by transcutaneous injection before, during or after treatment in order to enhance the effectiveness of the microwave applicator. Exemplary substances include those that change the local dielectric or conductivity properties of fat, change blood perfusion, sensitize the fat to thermal damage or modify the biological response to injury.

BRIEF DESCRIPTION OF THE DRAWINGS

These and other features and advantages of the present invention will be better understood from the following detailed description of an illustrative embodiment when read in conjunction with the accompanying drawings, in which:

FIG. 1a is a schematic diagram of an alternate embodiment of the microwave applicator of FIG. 1;

FIG. 2 is a schematic diagram depicting skin with its adnexa, the subcutaneous fat layer, and a portion of the underlying muscle layers;

FIGS. 4 and 4A are diagrams of a typical arrangement of antenna elements in the microwave applicator of FIG. 1;

FIG. 19 is a diagram of a circuit employing microwave detectors for monitoring operation of the system.

DETAILED DESCRIPTION

Figure 1:
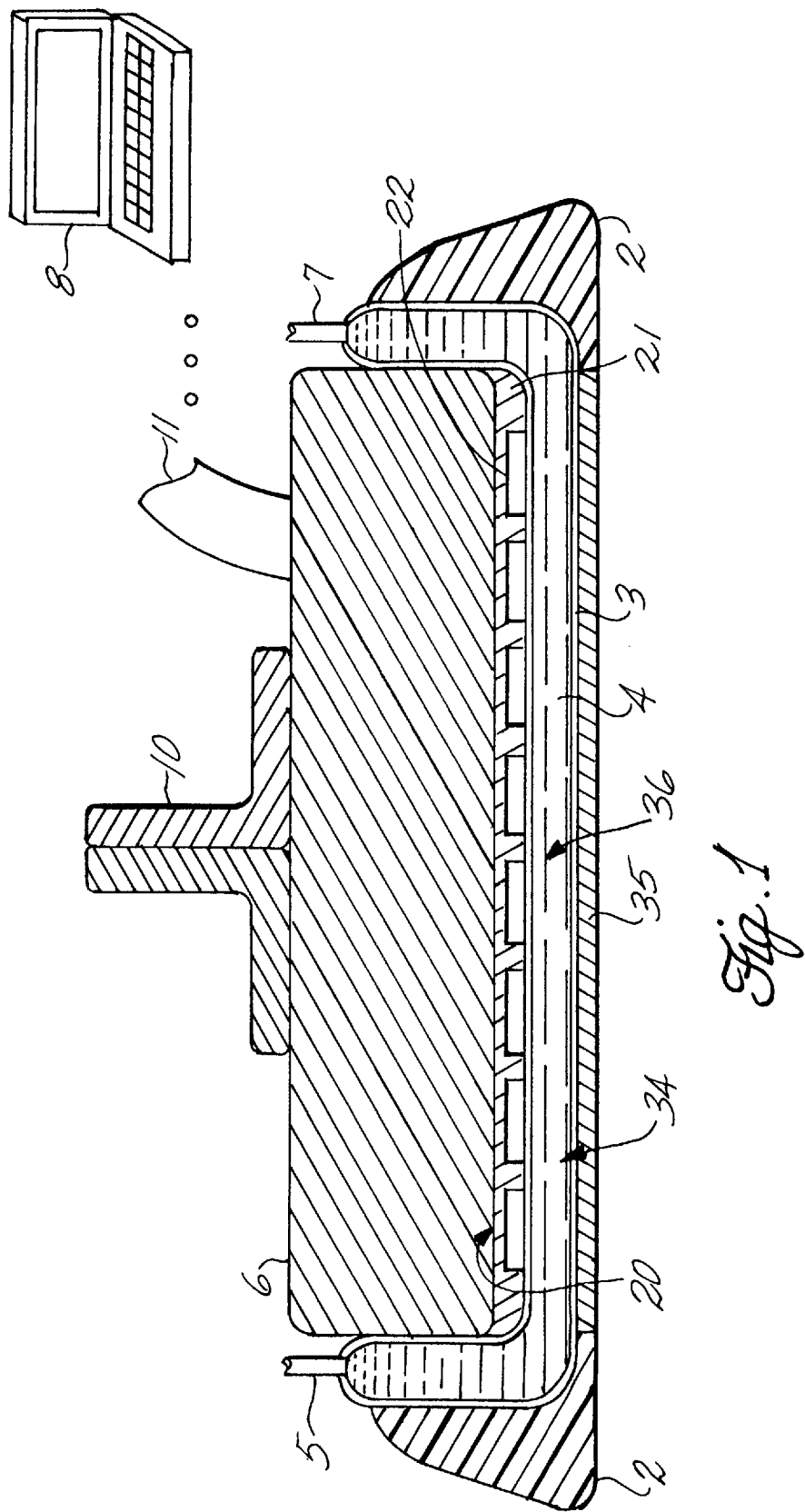
FIG. 1 is a schematic diagram, partly in cross section, of a general purpose therapeutic microwave hyperthermia applicator according to the present invention for noninvasive application of a thermal dose to target tissue.

Referring to FIG. 1, a microwave applicator for inducing hyperthermia in target cells includes an antenna element array 20 having individual antenna elements 22 embedded in a ground plane 21. The array is coupled to an electronic housing, or feed distributional manifold 6, for enclosing electronic components and circuits required for production and control of microwave power. Computer control signals, bias voltages, amplifier power, and possibly microwave power carried through transmission lines are bundled in one or more flexible conduits 11. A control system including a digital computer 8 operating under the direction of control software is coupled to the applicator through the conduit. A watch-dog circuit can be implemented that requires a periodic signal from the controlling computer. If it fails to receive the signal, the applicator can be shut down by the watch-dog circuit for safety. It will be understood by those skilled in the art that the control system may be incorporated on firmware located on the applicator unit itself or at a remote location.

For cooling the skin surface during microwave application, the applicator further includes a two-layered bolus 34. In one embodiment (see FIG. 1), a low-impedance layer 35, contacting the skin surface, is formed of a solid high-dielectric material, such as ceramic. The range of dielectric constants suitable for the low impedance is from about 30 to about 90. A preferred range is from about 70 to about 80. A high-impedance layer 36 is formed of a thin-walled, low-or-high-dielectric constant vessel 3 through which a cooling fluid 4 is circulated by way of fluid inlet and outlet ports 5, 7. The cooling fluid is chosen to have a dielectric constant much lower than that of the low-impedance layer. The range of dielectric constants suitable for the high-impedance layer is from about 4 to about 7. A preferred range is from about 5 to about 6.

The solid portion of the bolus for this embodiment of the applicator is preferably thin-walled but does not have to be flexible. The liquid portion of the bolus is preferably non-toxic, and should have sufficiently low viscosity so as to allow it to be pumped through the bolus at a rate sufficient for thermal transfer. One suitable liquid includes a mixture of an oil and a polar solvent. The liquid is preferably collected by a return manifold and distributed to cooling tubes in close proximity to heat generating electronics for active cooling of the electronics.

To absorb surface waves incident on the ends of the bolus, part of the high-impedance bolus layer is directed upward along the side of the electronic housing to trap the waves. In addition, the ends of the low-impedance layer are integrally connected to a bounding ring of absorbing terminators 2 made of lossy absorbing material for absorbing power in the surface waves incident on the truncation of the applicator. In operation, the bolus acts as a heat exchanger to maintain the temperature of the skin surface below about 120° F. Above this temperature, unwanted damage to cells proximate the skin surface may occur. Preferably, the skin surface temperature is maintained below 113° F. to prevent discomfort. In addition to acting as a heat exchanger, the bolus also conditions the microwaves as they pass from the antenna array through the bolus, and helps to focus the microwaves. For optimal conditioning and focusing, the various dielectric constants of the components within the bolus are preferably uniform.

Referring to FIG. 1a, in another embodiment of the applicator, the low-impedance layer 38 of the bolus is formed of a high dielectric shell 40 proximate the skin surface through which a high-dielectric cooling fluid 42, such as water, is circulated. The high-impedance layer 44 is formed of a solid lower dielectric material, such as a polytetrafluoroethylene, barium titanate matrix, or by a ferrite material. In the alternate embodiment, the range of dielectric constants suitable for the low-impedance layer and the high-impedance layer are the same as those for the preferred embodiment described above.

A principle of operation of the microwave applicator is to generate a plurality of cylindrical quasi-transverse electromagnetic surface waves proximate the target tissue. Through successive phase shifts, the waves are brought to convergence, thereby producing a column of high power density within the target tissue. The effect of the column of high power density is to raise the temperature of target tissue to a level at which cell necrosis or induction of apoptosis occurs.

FIGS. 4 and 4A show the underside of the antenna element array 20 that is part of the microwave applicator comprising a ground plane 21 and individual antenna elements 22.

Figure 5:
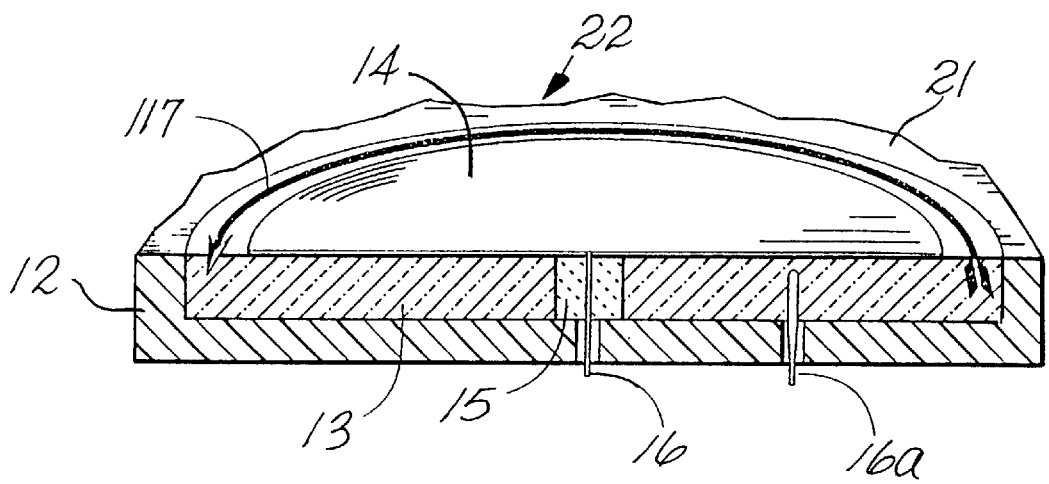
FIG. 5 is a diagram of a typical antenna element used in a preferred embodiment of the present invention.

Referring to FIG. 5, in a preferred embodiment, the individual antenna elements 22 of the array consist of circular microstrip antennas recessed into the ground plane 21 so that the circular patch 14 is flush with the surface of the ground plane. The elements are fed via a coaxial feed 16 at the geometrical center of the patch through a dielectric or ferrite cylinder 15, whose electrical properties and diameter are chosen along with the electrical properties of the substrate dielectric 13 to cause the element to resonate at the desired operating frequency.

An electric vertical monopole-like mode is produced by the element with an equivalent magnetic current 117 in the gap between the path edge and the ground plane that is uniform in the azimuthal direction. Additional matching of the final amplifier stage is accomplished, if necessary, through an additional conventional matching network to which the coaxial feed 16 is attached. The interior field under the patch, which is proportional to the strength of the equivalent magnetic current 117 (which determines the radiating properties of the element), is sampled via capacitive coupling by the weakly coupled coaxial port 16a. The purpose of the coaxial feed and the feedback loop is to obtain actual data during operation of actual phase and amplitude. The coaxial feed allows measurement of actual phase and amplitude.

Figure 6:
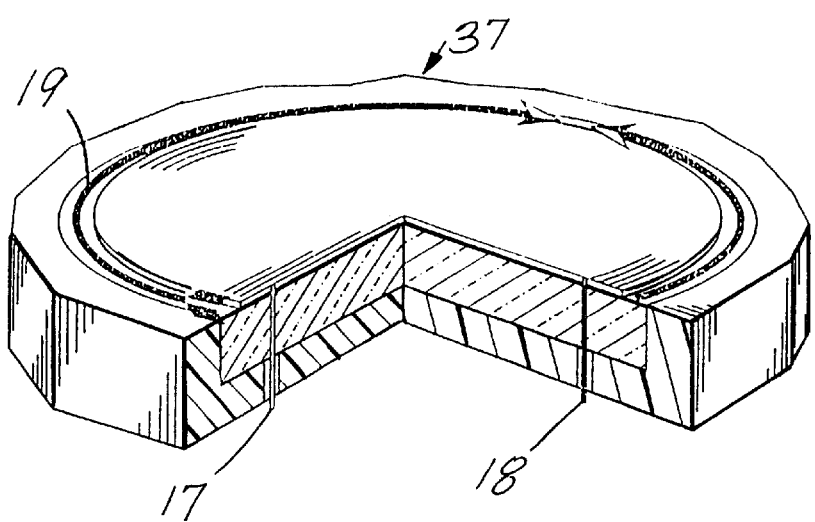
FIG. 6 is a diagram of an alternate embodiment of antenna element.

Referring to FIG. 6, in an alternate preferred embodiment, a dual-feed circular patch antenna 37 is disclosed. The dielectric properties of the substrate material are chosen in this embodiment to resonate the element in a horizontal dipole-like mode. In this mode, the equivalent magnetic current 19, produced when the antenna is fed at coaxial feed port 18, undergoes a change in direction along a nodal plane that bisects the circular patch. A second coaxial feed 17 is placed in this nodal plane. The second feed is capable of independently exciting a similar magnetic current distribution rotated, however, 90° about the center of the patch. This rotated magnetic current produces an electric field in tissue whose transverse component (the component parallel to the plane of the patch) is orthogonal to the corresponding component produced by the other feed. Thus, by simultaneously feeding ports 17 and 18, any state of polarization can be produced.

The first embodiment described above has the advantage of simplicity, requiring half the number of amplifiers, feed ports, and phase shifters as the alternate preferred embodiment. It also has the advantage of producing only substantially transverse magnetic fields. This is an electromagnetic field which lacks a component of magnetic field perpendicular to the plane of the patch. In contrast, the alternate embodiment produces both transverse magnetic and transverse electric field types, the latter of which lacks the desired component of electric field normal to the tissue planes. FIG. 4a illustrates the direction of average magnetic current in each of the elements that would have to be synthesized using appropriate amplitude and phase adjustment of the two ports of the dual-polarized element to launch a converging quasi-TEM cylindrical wave at the focal line 26. The required direction is obtained by constructing a line 24 between the projection 25 of the focal line 26 onto the aperture plane and the center 27 of a given dual-polarized element. The average required direction of magnetic current 23 is then perpendicular to the line 24. Thus, as the scan point varies within the target tissue, the polarization of the dual-polarized elements likely will have to be readjusted. This embodiment, however, has the advantage of flexibility for use in various target tissue, including tissue in the adipose layer, or other target tissues or tumors in deeper tissue layers.

Figure 7:
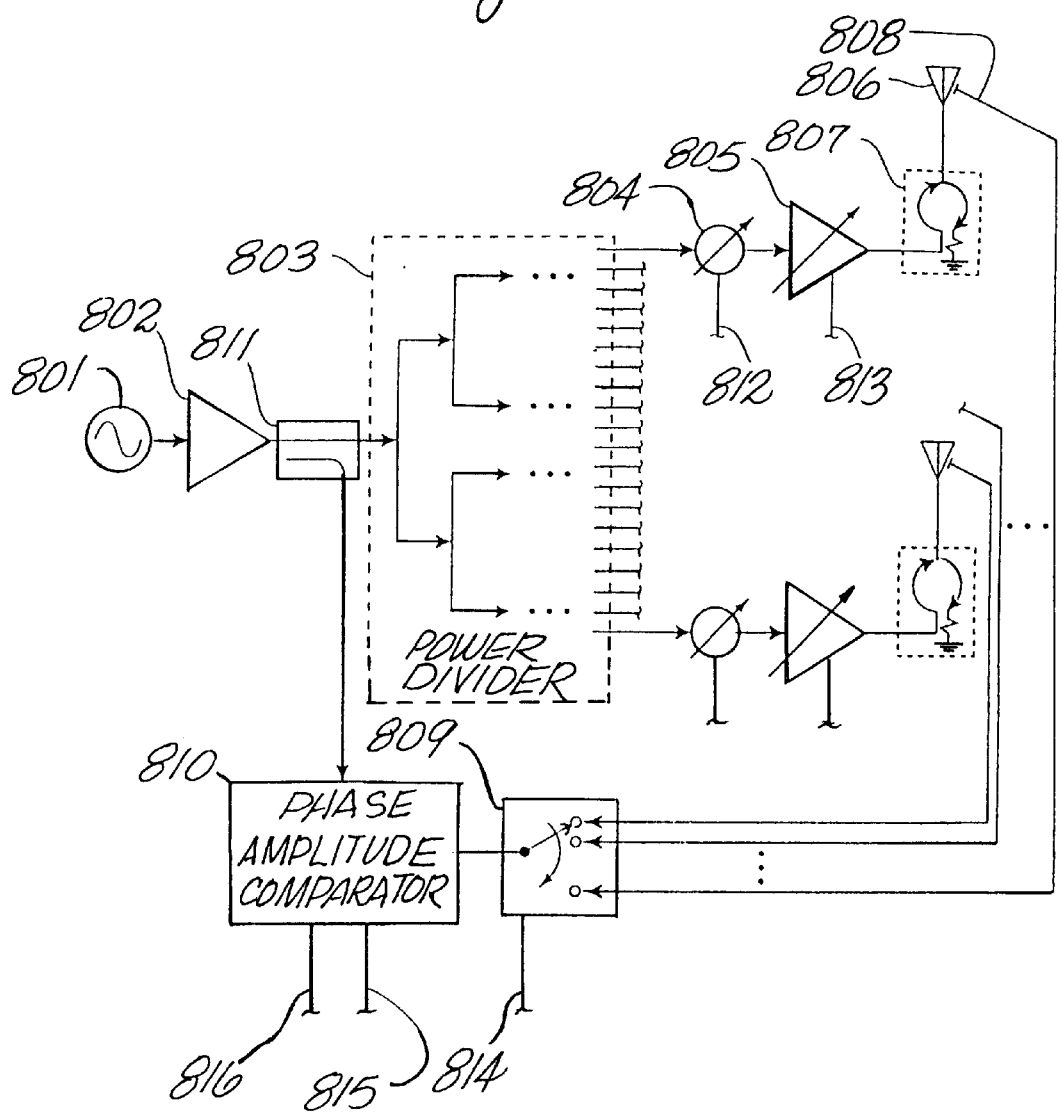
FIG. 7 is a circuit diagram of an exemplary antenna element feed and control system.

The overall system design of the exemplary embodiment using antenna elements 22 as shown in FIG. 5 is illustrated in schematic form in FIG. 7. The output of a common fixed-frequency oscillator 801 is amplified through a fixed gain amplifier 802, whose output is sampled by a directional coupler 811. The output of the main branch of the directional coupler is split by a power-divider 803. This provides a phase-coherent input signal to each of the phase shifters and amplifiers that feed the radiating antenna elements. For example, the output of one branch of the power divider feeds a 0–360 degree variable-phase shifter 804 controlled by the dc control voltage in biasing line 812. The output of the phase shifter enters a variable gain amplifier 805, whose gain is controlled by dc control voltage on a biasing line 813.

Depending on the voltage-standing-wave mismatch tolerance of the final output transistor in the variable-gain amplifier 805, an isolator 807 may or may not be included. The output of the amplifier or the isolator, if present, is fed to the input port of an antenna element 806 (element 22 in FIG. 5). The total internal field of the antenna element, which depends both on the actual feed voltage applied to its own input and on the mutual coupling between other antenna elements in the array, is sampled through a weakly coupled sample port 808 (element 16a in FIG. 5). This signal is coupled through a single pole, multithrow microwave switch 809, which is controlled by a control signal on line 814 to a phase-amplitude comparator 810. This comparator sequentially compares the phase and amplitude of each antenna to the phase and amplitude reference provided by the coupled port of the phase shifter. The phase and amplitude of each antenna are output as dc voltage levels on lines 815 and 816. This information is provided to the controlling computer through analog-to-digital converters. By using an appropriate control algorithm, the bias voltage levels on the phase shifters and the variable-gain amplifiers can be adjusted so that the actual amplitude and phase of the antenna array elements are brought to their desired nominal levels. It will be understood to those of ordinary skill in the art that individual phase comparators, such as I.Q. demodulators, can be provided for each individual antenna.

Although the disclosed feedback system provides the controlling computer 8 with measured amplitudes and phases of the antenna elements, a sufficiently stable system can be operated without phase feedback information. A phase calibration measurement is done for each channel using a representative tissue phantom in the presence of the bolus. The calibration data is then used to adjust the phase-shifter bias voltages and gain voltages during actual operation of the applicator. In this method, periodic calibration checks are used to ensure that the actual phases and amplitudes produced in the applicator antennas are not significantly different from those that are desired.

Figure 7A:
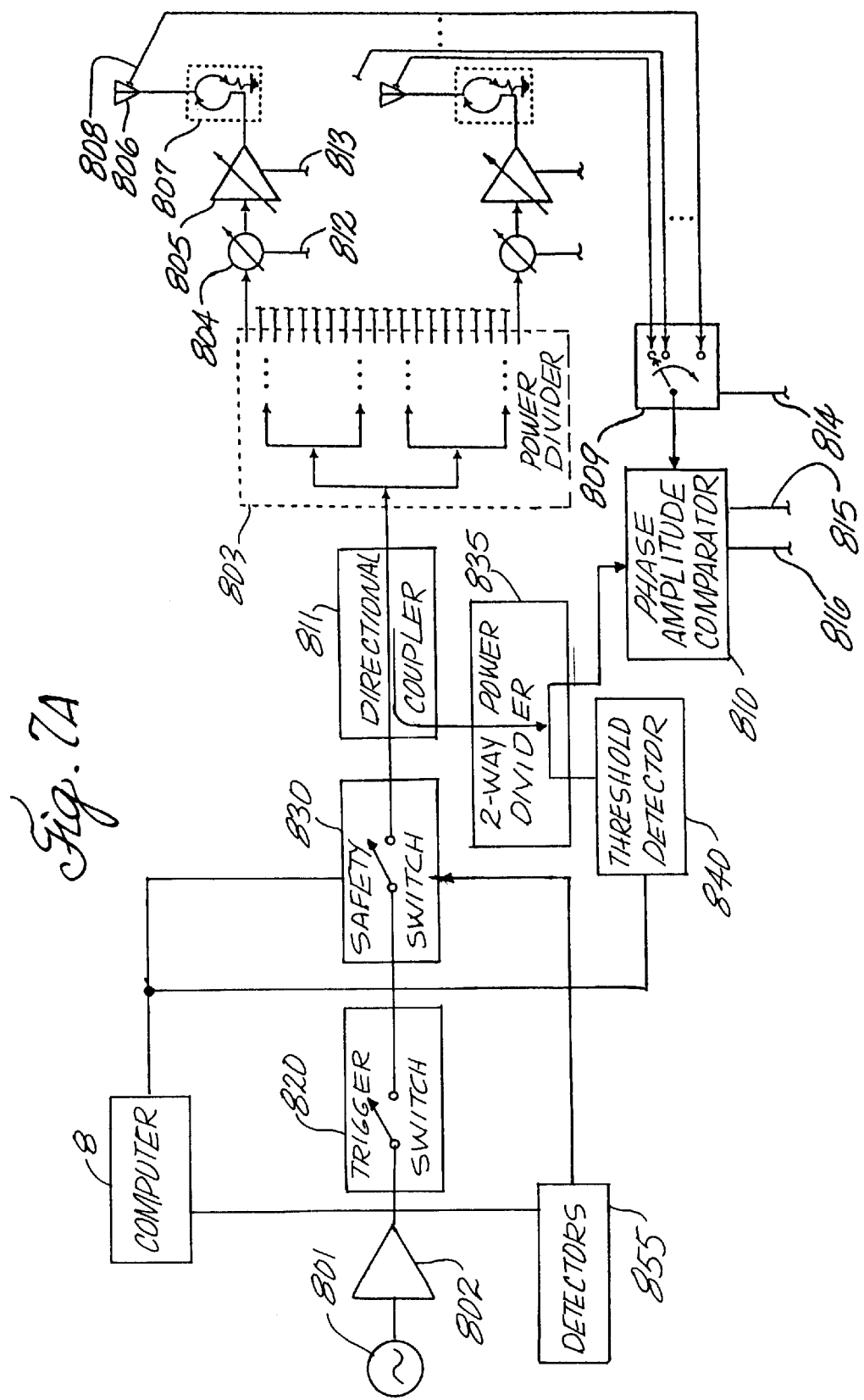
FIG. 7a is a circuit diagram of an alternate embodiment of the feed and control system of FIG. 7, incorporating a novel switching circuit.

Referring to FIG. 7a, an alternate embodiment of the circuit disclosed in FIG. 7 includes a trigger switch 820 and a safety switch 830 connected in series between the oscillator 801 and power divider 803. The trigger switch is coupled to the controlling computer 8. The trigger switch starts and stops the microwave treatment pulse, and the safety switch, when closed, enables power to be delivered to the patient. In operation, the control computer instructs the independent timer 855 to deliver a pulse. By the pulse, the timer closes the safety switch 830 for a period of time that is predetermined and not controllable by the computer 8. After the safety switch is closed, a signal is sent by the computer 8 to close the trigger switch, thereby beginning the treatment pulse. At the end of treatment pulse, a terminating signal is sent by the computer to open the trigger switch 820, thereby preventing power from reaching the antenna array. If the trigger switch fails to open within the predetermined period, the safety switch will independently open after the predetermined time set by the independent timer pulse, thereby terminating the treatment.

As an additional safety mechanism, a threshold detector 840 samples the power incident on the power divider 803. In operation, the sampled power is divided by the two way power divider 835, a portion of which is delivered to threshold detector 840. The computer monitors the threshold detector to determine whether power is being supplied to the power divider 803. If the computer detects that power is still being supplied to the power divider 803 after the trigger switch 820 was supposed to open, then the computer shuts down the treatment system.

Referring to FIG. 19, operation of the system can be checked by employing microwave detectors 855 and applying signals to selected subsets of elements (for example, pairs of elements). In this method, a sequence of excitation amplitudes and phases is first applied such that the power absorbed in the presence of the bolus and tissue phantom by a third selected antenna is substantially null. A failure of one or more of the elements of the selected subset of elements to produce the nominal amplitude and phase to effect this null response is then detected. By systematically choosing different subsets of elements, the specific elements whose amplitude and phases deviate from the nominal is identified and the user alerted via the controlling computer 8 of the need for recalibration or repair of the affected channels. The method can be implemented as a routine self-check procedure done periodically, e.g., each morning before clinical use. The method of choosing the appropriate excitation to produce a null in reabsorbed power by a chosen antenna is similar to that suggested by using null-space projections of excitations as disclosed below. The detectors used for this purpose can be the same detectors 402 as those set forth in FIGS. 11 and 12 for circuit protection.

Figure 8:
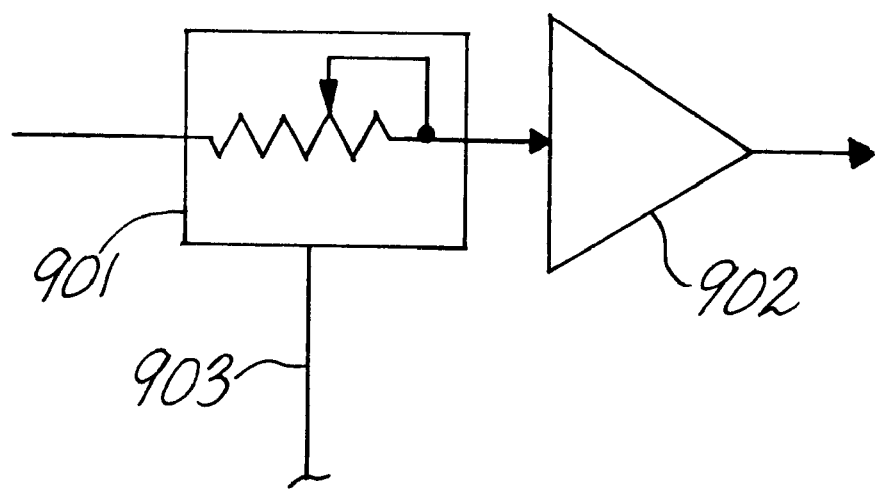
FIG. 8 is a diagram of how to realize the variable gain amplifiers in FIG, 7 using a variable attenuator and a fixed-gain amplifier.
Figure 9:
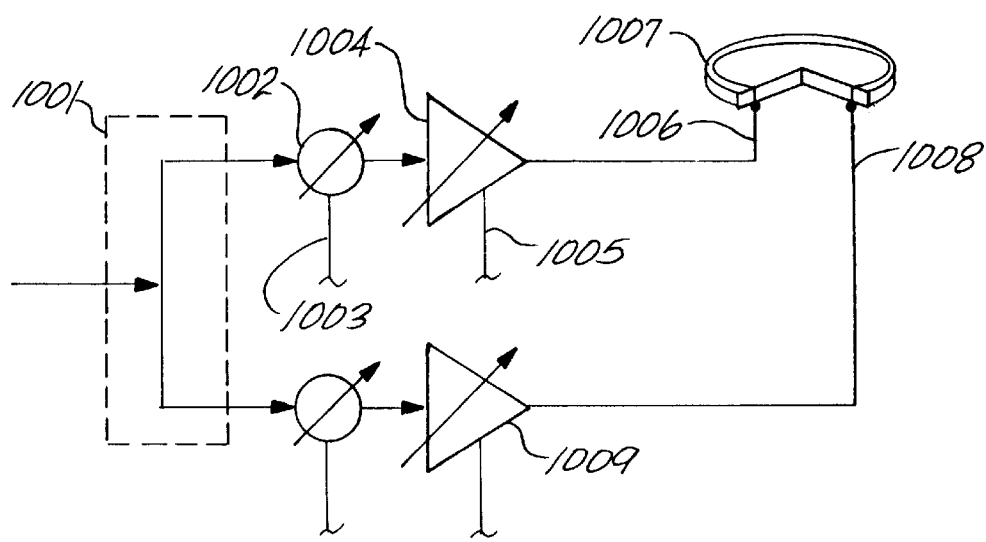
FIG. 9 is a circuit diagram of another exemplary control system for activating particular antenna elements of the type illustrated in FIG. 6.
Figure 9A:
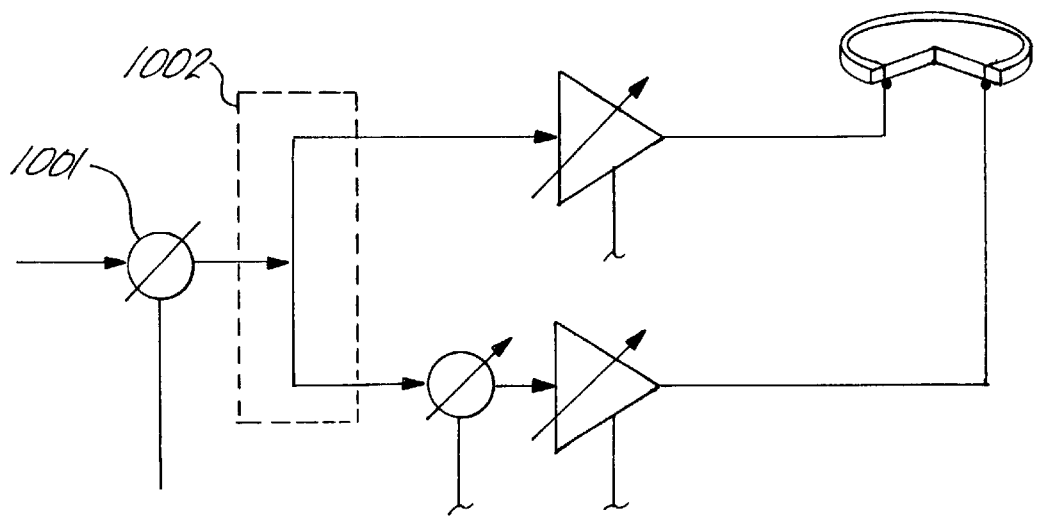
FIG. 9a is a circuit diagram of an alternate embodiment of the control system of FIG. 9.

The output power of the variable-gain amplifiers can be controlled by adjusting the bias voltage on one or more amplifier stages through control voltage lines provided in commercially available power modules. Alternatively, the attenuation of a voltage-controlled analog or step attenuator 901, illustrated in FIG. 8, can be controlled by the bias voltage placed on biasing line 903. The output of this attenuator feeds the input of a fixed-gain amplifier 902. Use of the alternative antenna element 37 illustrated in FIG. 6 may require the feed network illustrated in FIG. 9. In this case, the output of the main power-divider manifold 803 of FIG. 7 is further divided by a two-way power splitter 1001. The output of each port of the power splitter feeds two identical phase-shifter/amplifier combinations. For example, the output of one port feeds a voltage-controlled variable phase shifter 1002 with bias line 1003. The output of the phase shifter feeds the variable-gain amplifier 1004 with control-voltage line 1005. The output of one amplifier feeds one of the two feed ports 1006 (element 17 in FIG. 6) of a dual-polarized circular microstrip antenna 1007 (element 37 in FIG. 6). The output of the other amplifier 1009 feeds the second orthogonally placed feed port 1008 (18). By adjusting the amplitude and phase of each of the two branches, the net power in each of the two orthogonal polarizations that the antenna element 1007 (37) produces can be independently adjusted, yielding the desired polarization state at the desired amplitude and phase. Alternatively, one of the phase shifters 1001 can be placed between the output of the main power-divider manifold 803 of FIG. 7 and the two-way power divider 1002, as illustrated in FIG. 9a.

Figure 10:
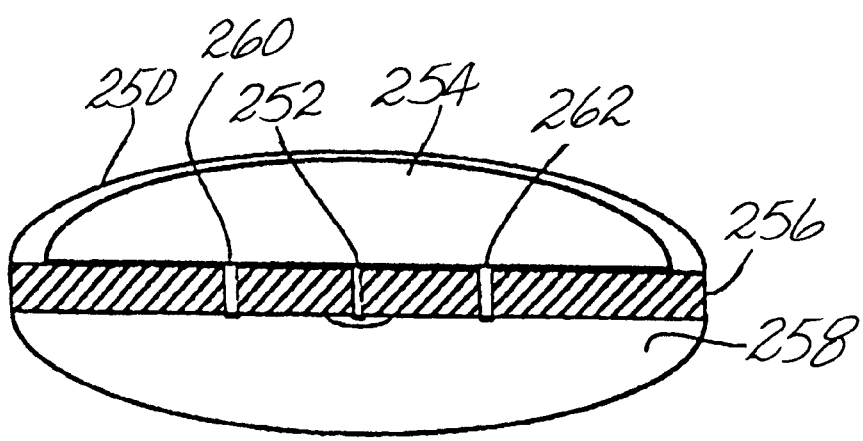
FIG. 10 is a perspective view, partly in cross section of a monopole-like circular microstrip antenna.

Referring to FIG. 10, in another embodiment of the present invention, a monopole-like circuit microstrip antenna 250 enables adjustment of its resonant frequency and impedance match. The antenna is fed at its geometrical center via an extension of the center pin 252 of a coaxial transmission line and is electrically connected to a preferably circular-shaped metal top patch 254 which is insulated by a physical gap 256 from the ground plane 258. A pair of short-circuiting pins 260, 262 are placed symmetrically about the center feed 252. The diameter of the shorting pins and their radial location from the center of the antenna are used together to adjust the resonant frequency of the antenna element to the operating frequency of the array and to adjust the input impedance of the antenna at the operating frequency to approximately 50 ohms in the preferred embodiment. Adjustment is preferably made in the presence of the bolus and tissue-equivalent phantom and with all other antennas ports loaded with 50 ohms. As the diameter of the pins becomes smaller, the effective inductive loading of the antenna becomes higher and the resonant frequency becomes lower. The closer the shorting pins are to the center feed, the more undercoupled the Smith-Chart plot of the antenna impedance will become. More than two shorting pins lying a fixed radius from the center feed and equally spaced in angle about the center feed can be used providing a more symmetrical voltage distribution in the gap between the circular metal top patch 254 and the ground plane 258. It will be understood that the same or similar principles can be employed by those skilled in the art to design antennas for this application of noncircular shape such as hexagonal, triangular, or square antennas.

Figure 11:
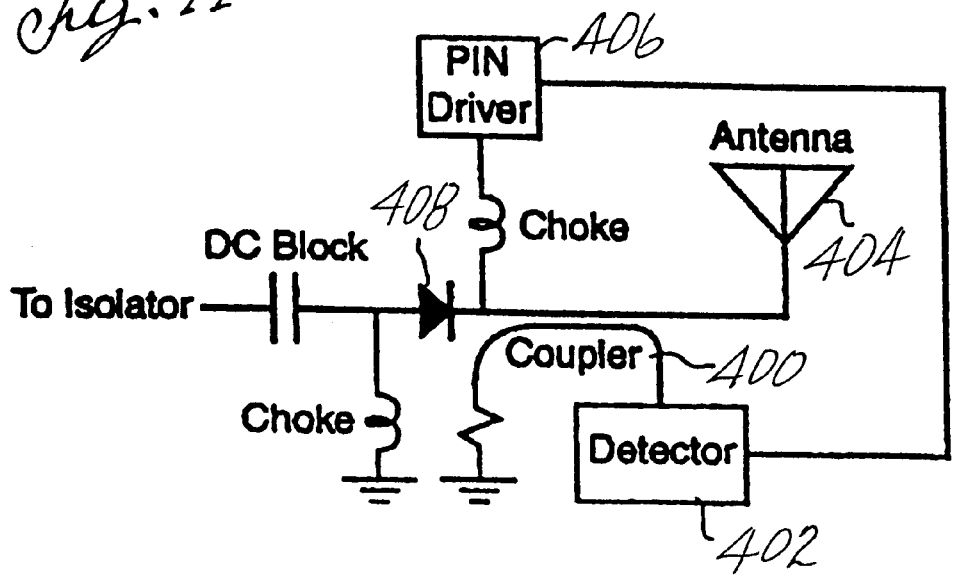
FIG. 11 is a diagram of a circuit for protecting the antenna elements from reabsorbed power.
Figure 12:
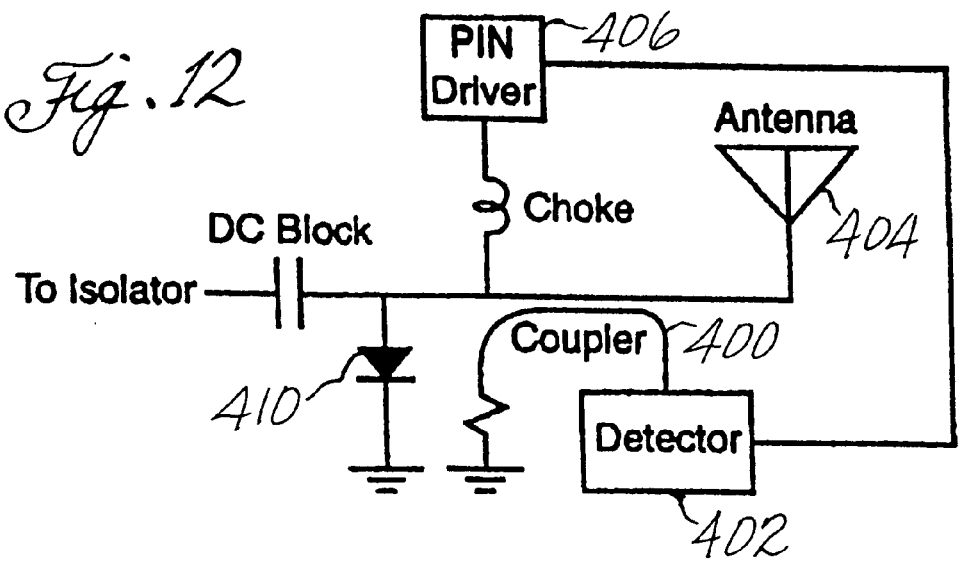
FIG. 12 is a diagram of an alternate embodiment of a circuit for protecting the antenna elements from reabsorbed power.

Referring to FIGS. 11 and 12, in which like reference numerals are used to define like parts, two circuits are disclosed for protecting antenna elements from reabsorbed power. During operation of the applicator, the mutual coupling between antenna elements can be large with an otherwise optimally chosen bolus. The amount of reabsorbed power can be particularly high in the antenna, over a focus that projects onto an antenna, or in the antennas nearest the focus when the focus projects between antennas. The reabsorbed power level can be sufficiently high to damage components within the channels connected to the affected antennas. The protection circuits generally include a directional coupler 400 and detector element 402, which detects the power reabsorbed by the i-th antenna 404. If the detected power level exceeds a set threshold, then a PIN driver circuit 406 is triggered biasing the PIN diodes to an open state in the case of a series PIN diode 408 (FIG. 11), and to a conducting state in the case of a shunt PIN diode 410 (FIG. 12). The placement of the PIN diodes for either series or shunt configurations can be arranged so that the discontinuity it generates when triggered reflects as a short circuit across the gap between the microstrip antenna element and the ground plane, thus making the "removed" antenna appear as a continuous and nonperturbing ground plane. This method of removing the antenna from the circuit for circuit protection is illustrative. Those skilled in the art can design other circuits based on this principle. For example, the controlling computer, rather than a detector circuit, can trigger the PIN diode state, and other types of switches rather than PIN diodes may be used.

Figure 13:
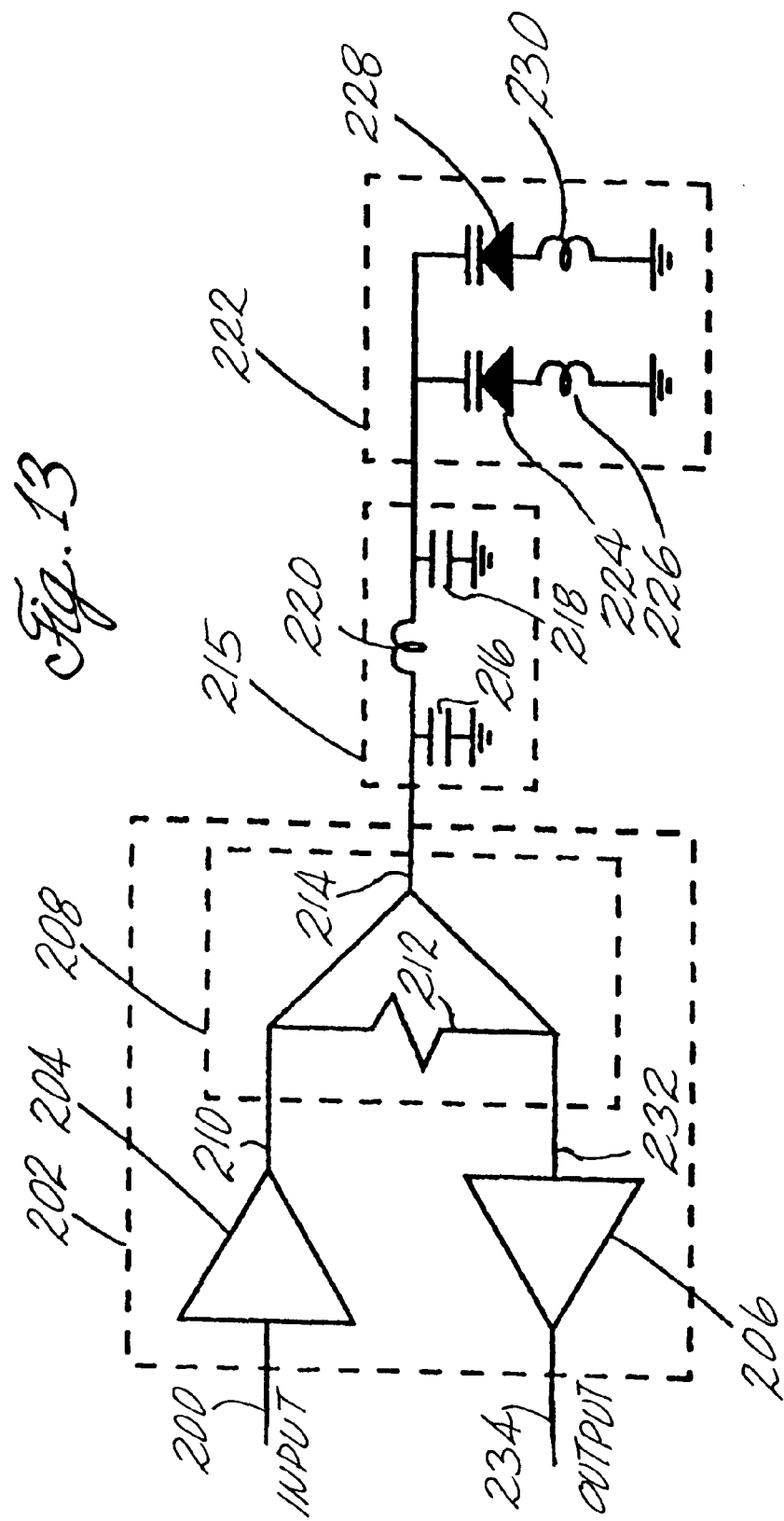
FIG. 13 is a circuit diagram of presently preferred embodiment of a phase shifter for operating the applicator.

Referring to FIG. 13, a presently preferred embodiment of a phase shifter for operating the applicator is a novel modification of a reflection-type analog phase shifter based on a reactively loaded circulator. In operation, the signal enters the input port 200 of the phase shifter to an amplifier circuit 202 including first (input) and second (output) unidirectional amplifiers 204, 206 connected to two way power divider 208. The signal is amplified by the first unidirectional amplifier 204 and enters an output port 210 of the two-way power divider 208. Approximately half of the power is lost in the compensating resistor 212 within the power divider while the remaining half of the power leaves the divider through input port 214. The signal goes through the compensating circuit 215, which includes a pair of capacitors 216, 218 coupled off the main signal path to ground, and an inductor 220 on the main signal path. The compensating circuit is designed to reduce amplitude variation as a function of phase. The signal from the compensating circuit then impinges upon the load circuit 222. The load circuit includes a parallel combination of a first series combination of a varactor diode 224 and inductor 226 and a second series combination of a varactor diode 228 and inductor 230, which may be implemented as a shorted transmission line or as a discrete inductor. The inductance in one of the series combinations may represent the varactor case inductance and the inductance associated with directly shorting the varactor. The inductance in the other series combination of a varactor and inductor is preferably chosen to be different from its counterpart in the other series circuit. The entire load circuit 222 is designed so that within the tuning range of the varactors, the load impedance completes a full circle or more within the Smith Chart.

The signal reflects off of the load circuit 222 with a phase shift of between 0 and 360 degrees that depends on the bias voltage applied to the varactors. The signal again goes through the compensating circuit 215 whereupon it reenters the input port 214 of the two-way power divider 208. Half of the power impinges on the output port of the input amplifier 204. Because of the low reverse gain of the input amplifier 204, only a small amount of the signal leaves the input port 200 of the input amplifier, thus yielding a low VSWR at the input of the phase shifter. The other half of the power impinges on the input port 232 of the output amplifier 206 whereupon it is amplified and presented at the output port 234 of the phase shifter.

Since the varactor diodes 224, 228 in the load circuit 222 are not perfect voltage-controlled capacitors, but instead have some series resistance, the insertion loss of the phase shifter is strongly dependent on the varactor bias voltage which causes the phase shift. The finite isolation of the two-way power divider 208 also adds to the imbalance in insertion loss as a function of bias voltage. This manifests itself as a shifting of the center of the circle in the Smith Chart representing the impedance of the load circuit 222 from the center of the Smith Chart. With the proper adjustment of the reactive elements of the compensating circuit 215, the impedance looking into the load through the compensating circuit can be centered in the Smith Chart thus minimizing the variation of insertion loss with phase shift.

Those skilled in the art would readily appreciate that the phase shifter circuit can vary without departing from its function. For example, the compensating circuit could be implemented as a fixed transmission line of appropriately chosen characteristic impedance and length, or it could have other topologies of discrete reactive or resistive elements or combinations of transmission lines and discrete elements. The output amplifier is not strictly required in the design of this phase shifter, but generally provides additional isolation between input and output and increases the overall gain of the device.

To reduce the variation in insertion loss versus phase shift that must be compensated by the compensating circuit 215, the isolation of the two-way power divider 208 is preferably chosen as high as possible, and ideally greater than about 30 dB, although isolations of as low as 20 dB or lower are acceptable. If the output amplifier 206 can be driven in saturation, the insertion loss variation with respect to phase shift can also be reduced. Attenuators between the output 210 of the input amplifier 204 and the two-way power divider 208, and between the input 232 of the output amplifier 206 and the two-way power divider 208 can be added to adjust signal levels and provide additional isolation.

Although it will be understood that conventional phase shifters may be adapted to operate the antenna array, the advantages the phase shifter disclosed herein over conventional reflection-type phase shifters include: replacement of typically much more expensive and larger circulators; a gain generally larger than unity instead of a positive insertion loss as seen with circulator-based (or similar quadrature-hybrid based) phase shifters; saturation of the output amplifier that can reduce output amplitude variations versus phase; and minimization or reduction of variations in output signal versus phase shift.

The general purpose microwave applicator according to the present invention is useful for inducing hyperthermia in a variety of applications. One straightforward application involves using the microwave applicator to treat tumors. Another such application involves the use of the microwave applicator to reduce adipose tissue.

Adipose tissue, more commonly known as fat, is formed of cells containing stored lipid. In humans, adipose tissue is widely distributed in subcutaneous tissue located between an outer skin layer and inner muscle layers. Fat cells are relatively large, ranging up to 120 microns in diameter. An excess of adipose tissue, a condition known as obesity, may be undesirable in that it gives rise to various health problems in human beings, both physical and psychological. The former includes an increased risk of heart disease, high blood pressure, osteoarthritis, diabetes, and other unhealthful conditions. The latter can result in a deterioration of an individual's self image and work and social relationships because excess fatty deposits may be perceived by the individual, and those with whom the individual interacts, as having an unsightly appearance. Dieting and behavior modification are helpful for reducing body fat, but it is often difficult to differentially remove fat from selected areas of the body, such as the abdomen or buttocks, while retaining desirable fat in other parts of the body. Moreover, many cannot maintain the regimen of sustained dieting combined with exercise to remove undesired fat from these areas. In such circumstances, spot fat reduction may be needed to eliminate relatively localized fat deposits that may be otherwise difficult to remove by dieting or exercise.

Figure 3:
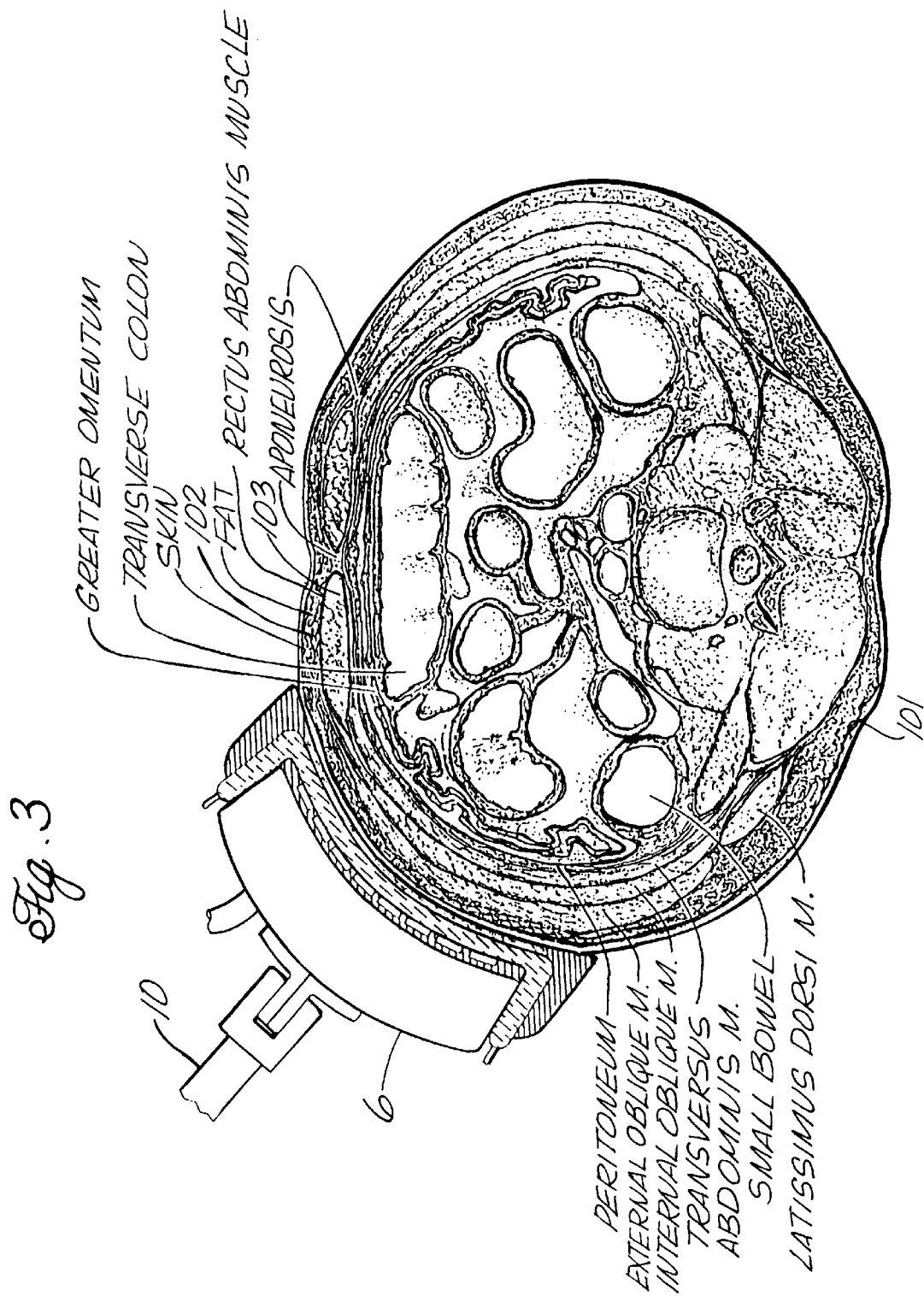
FIG. 3 is a diagram of a microwave applicator according to the present invention and a cross-sectional view of a typical human abdomen showing the skin, subcutaneous fat layer, underlying muscle layers, and viscera in conjunction with a microwave applicator according to the present invention.

The microwave applicator according to the present invention can be used to effectively remove fat cells by inducing hyperthermia in the adipose layer without the use of significantly invasive procedures and without any substantial damage to surrounding normal tissue in the adjacent skin and muscle layers. FIGS. 2 and 3 show cross-sections of a typical human body showing the skin layer 101, the muscle layers 103, and the fat layers 102. Also shown are the skin-fat interface 104 and the muscle-fat interface 107. For fat removal, a principle of operation of the present invention is the generation of a cylindrical converging quasi-transverse electromagnetic surface wave within the fat layer by taking into account the differing dielectric constants and heat capacities of the tissues in the adjacent skin and muscle layers. As shown in FIG. 3, the microwave applicator may be designed with a curved surface to fit against body contours.

The antenna element arrays shown in FIGS. 5 and 6 are both sufficient to induce hyperthermia in the adipose layer. The embodiment of FIG. 5 produces an electric field component that is perpendicular to the plane of the patch, which is important for the application of preferentially heating the fat layer. The embodiment of FIG. 6 is useful for treating deeper tissues, although it can be used for heating the fat layer by coupling to converging cylindrical waves.

In an exemplary embodiment, assuming a fat layer thickness of 3 cm, the dimensions of the bolus are about 21 cm×21 cm. In a preferred embodiment, optimal excitations for the antenna elements are determined as a function of fat-layer thickness and the dimensions of the bolus. The dimensions of the housing for the exemplary embodiment are about 20 cm×20 cm and the overall dimensions of the antenna array are about 15 cm×15 cm. In the exemplary antenna array, there are 73 individual antenna elements. Each antenna element has a radius of approximately 0.76 cm and is about 1–2 mm thick. Preferably, the overall dimensions of the array should be as small as possible to provide spot fat reduction in hard-to-reach areas while still being effective to launch a converging cylindrical surface wave within the fatty layer. This, of course, may vary depending on the use of the applicator. In general, a limiting constraint for the dimensions of the bolus is the radius of the antenna element. The thickness of the bolus is chosen to optimally condition the microwaves while effectively cooling skin surface during application.

The present invention includes a control system for choosing optimal antenna array excitation during operation of the applicator. In an exemplary embodiment, the control system includes a software driven digital computer coupled to the amplitude and phase control circuit of the antenna array. For an N element array in which the voltage applied to the $i^{th}$ antenna element is $V_i$, the column matrix of N such excitations in the array is:

$$V\rangle = \begin{pmatrix} V_1 \\ V_2 \\ \vdots \\ V_N \end{pmatrix}. \tag{I}$$

In this disclosure, bracket notation is employed wherein a symbol appended with ">" denotes a column matrix, while the same symbol prepended with "<" denotes the complex conjugate transpose (a row matrix) of the same matrix. Defining the efficiency η of the excitation as the ratio of the power density at the indicated focal point divided by the total power radiated by the array at for example the surface of the bolus, there are at least two methods according to the present invention for determining optimal array excitation for use of the applicator.

The first, known as naive focus, involves a relatively simple method of focusing that provides a relatively high efficiency. To implement the method in practice, one chooses:

$$|V_i|=v_0,$$

$$\arg(V_i)=k|\rho_i^- \rho_f|, \tag{II}$$

where $v_0$ is a voltage level not exceeding that achievable by all of the array channels; $\rho_i$ is the two-dimensional position vector locating the center of the $i^{th}$ antenna element projected onto the surface of the bolus; k is the intrinsic wavenumber of the fat layer; and $\rho_f$ is the projected two-dimensional position vector locating the focus projected onto the surface of the bolus. This choice forces the phase fronts of cylindrical waves generated by antennas at approximately the same radial distance from the focus to interfere constructively at the focus. An advantage of this excitation is that it is relatively simple and has a relatively high efficiency. A disadvantage is that the peak power density occurs at the skin-fat interface and the power density decreases from that point monotonically to the muscle layer. This may cause discomfort in some patients due to heating of the skin layer adjacent the skin-fat interface.

A more general method of excitation, known as minimax excitation, enables adjustment of not only the focal position projected onto the bolus surface, but also the depth. In this method, a three-dimensional coordinate for the focal point $r_f$ is defined. $r_f$ is preferably chosen to lie within the fatty layer and at least a few millimeters to a few centimeters beneath the skin-fat interface. At a depth of a few millimeters, the vasculature proximate the skin-fat interface helps to allow infiltrate of macrophages and subsequent removal treated fat, but the focus of the heat is generally far enough from the interface to prevent skin damage and discomfort. Once the focal point is chosen, the system then solves a minimax problem:

Minimize by adjusting V<the maximum of P(r) over all points r in $\Omega$, (III)

where P(r) is the induced power density at observation point r and $\Omega$ is the volume containing substantially all of the tissues which have a risk of significant heating. In practice, this minimax problem is approximated by discretization with the introduction of a set $\Omega_M \subset \Omega$ containing a finite collection of M discrete sample points chosen at a sufficient density and at locations that ensure that no local field maximum at a point in set $\Omega$ will exceed significantly the field at the nearest sample points in set $\Omega_M$. The system defines a transition zone $\Omega_\delta \subset \Omega$ containing the focal point $r_f$ and substantially all points in some neighborhood of $r_f$ and ensures that $\Omega_\delta \cap \Omega_M = \Omega_f$, where $\Omega_f$ is the set of all focal points (which in the present case contains only the point $r_f$). A purpose of the transition zone is to allow the field near the focus to decay without necessarily burdening the optimization algorithm with the task of minimizing the field at points where it cannot be minimized significantly. The minimax problem is converted approximately to the nonlinear programming problem involving minimization of y with respect to V> subject to the following constraints:

$$P_1 = 1, \quad (IV)$$
$$\eta \geq \eta_{\min},$$
$$y \geq w_2 P_2,$$
$$y \geq w_3 P_3,$$
$$\vdots$$
$$y \geq w_M P_M,$$

where $P_i$ is the power density induced at the $i^{th}$ sample point; $w_i$ is the weight factor (normally chosen to be 1) at the $i^{th}$ sample point; $\eta$ is the efficiency; and $\eta_{min}$ is the minimum acceptable efficiency. In practice, one of the excitation coefficients V> has its phase set to an arbitrary value, for example 0°, to serve as a phase reference.

The weight factor $w_i$ may be used to allow the power density to increase (w<1) at points where this can be tolerated (such as the actively cooled skin surface) or decrease (w>1) at points where overheating may cause a problem or discomfort (such as pain generation at the skin-fat interface). In practice, the power density $P_1$ at the focal point $r_f$ corresponding to the first sample point is set to unity. Once a solution is obtained, then the solution V> is renormalized to the actual power level desired at the focal point consistent with the power available from the actual array and from individual array elements. So long as $\eta_{min}$ does not exceed the maximum efficiency $\eta_{max}$ for the given focal point, then the problem as described above is feasible and may be solved using conventional algorithms as successive quadratic programming or generalized reduced gradient techniques.

In an alternate embodiment of the minimax method, the optimization method can be amended to allow the placement of multiple simultaneous foci by minimizing y with respect to V> subject to the following constraints:

$$P_1 = 1, \quad (V)$$
$$P_2 = 1$$
$$\vdots$$
$$P_L = 1$$
$$\eta \geq \eta_{\min},$$
$$y \geq w_{L+1} P_{L+1},$$
$$y \geq w_{L+2} P_{L+2},$$
$$\vdots$$
$$y \geq w_M P_M,$$

where sample points 1 through L are foci.

As discussed above, mutual coupling between antenna elements may be large in this application in which a goal is to launch surface waves and achieve optimal spatial filtering of unwanted spectral components by the bolus. The power coupled into the antenna or antennas nearest the focus tends to be generally much larger than that coupled into any other antenna. If the power is sufficiently large, the isolators for that antenna and the amplifier circuitry connected to it may be damaged. It is thus desirable in some cases to limit the reabsorbed power to acceptable levels. Assuming the s-parameter matrix for the antenna array in the presence of tissue is denoted by S, then the fractional power reabsorbed by the $i^{th}$ antenna element to the total power incident on the array is:

$$F_i = |V_i^-|^2 / \langle V^+ V^+ \rangle = \frac{\langle V^+ S_i \rangle \langle S_i V^+ \rangle}{\langle V^+ V^+ \rangle}, \quad (VI)$$

where the total excitation of the array is V>=V$^-$>+V$^+$>; V$^-$> being the column matrix of signal voltage reflected back from the antennas toward the output ports of the amplifiers; V$^+$> being the column matrix of signal voltages incident on the antennas from the isolator outputs; and S$_i$> being the $i^{th}$ column of S. Thus the fractional returned power in the $i^{th}$ channel is the ratio of two hermitian quadratic forms, the denominator of which is positive definite and the numerator of which is a rank-1 positive semidefinite matrix. The matrix S$_i$><S$_i$ accordingly has one nonzero eigenvalue and corresponding eigenvector $\psi_i$>.

By projecting the excitation V$^+$> into the null space of $\psi_i$>, the reabsorbed power in the $i^{th}$ element is substantially eliminated, although the induced power density distribution in the tissue may be altered. One can also limit the maximum projection of V$^+$> onto $\psi_i$> thus limiting the amount of power reabsorbed into antenna i. Thus, one can introduce a reduction factor $1 \geq \xi \geq 0$, and create a new excitation $\overline{V^+}$> given by:

$$|\overline{V^+}\rangle = \left( I - \xi \frac{|\psi_i\rangle\langle\psi_i|}{\langle\psi_i\psi_i\rangle} \right) |V^+\rangle. \quad (VII)$$

Choosing $\xi=1$ eliminates the offending component of the excitation altogether and yields no reabsorbed power in the $i^{th}$ antenna element, and ξ=0 leaves the excitation unaltered. Any value of ξ in between is a compromise that will reduce the amount of reabsorbed power to some intermediate value. This principle can be extended to reduce or eliminate the power reabsorbed by more than one antenna, or the net reabsorption of power by the entire array. Accordingly, rather than modifying the excitation using null-space projections as presented above, the reduction in reabsorbed power can be introduced as a constraint directly into the optimization program by minimizing y with respect to V> subject to the following constraints:

$$P_1 = 1,$$ (VIII)
$$P_2 = 1$$
$$\vdots$$
$$P_L = 1$$
$$\eta \geq \eta_{min},$$
$$y \geq w_{L+1} P_{L+1},$$
$$y \geq w_{L+2} P_{L+2},$$
$$\vdots$$
$$y \geq w_M P_M,$$
$$F_{i_1} \leq \alpha_1,$$
$$F_{i_2} \leq \alpha_2,$$
$$\vdots$$
$$F_{i_K} \leq \alpha_K,$$

where $i_1, i_2, \ldots, i_K$ are the antenna-element numbers whose fractional reabsorbed power levels are to be limited by the positive constants $\alpha_1, \alpha_2, \ldots, \alpha_K$, respectively, and K does not exceed the total number of antenna elements N. These additional constraints may lead to unfeasibility of the nonlinear programming problem in cases where $\eta_{min}$ is chosen too large, or if K=N and the limits on reabsorbed fractional power are too low.

For antennas implemented as microstrip antennas, the actual physical entity that influences the induced field distribution within the tissues most directly is the average voltage induced between the edge of the metal patch and the closest point on the ground plane. The average voltage is the average loop magnetic current that can be used to model the antenna. Assuming $\upsilon_i$ denotes this average voltage on the $i^{th}$ antenna element, then $\upsilon_i$ would be proportional only to $V_i^+$ in the case where no mutual coupling occurred and the antennas were perfectly matched. However, the presence of imperfect antenna match and mutual coupling results in coupling of all $\upsilon_i$ to each $V_j^+$. This coupling is linear and is found to be predictable through simple quasi-analytical modeling. Thus, if υ> represents the column matrix of all average magnetic currents, then one can compute a matrix transformation Λ such that:

$$\upsilon > = \Lambda V >.$$ (IX)

In implementing the optimization algorithms disclosed above, the magnetic current used to compute the field induced in tissue by the antenna elements should preferably employ this transformation between the terminal voltage parameters V> and the magnetic current sources induced at the antenna boundaries υ>.

This final statement of the optimization problem for induced power density is illustrative of the method used to find the excitation voltages. Those skilled in the art can extend this statement of the optimization program through modification of the constraints or addition of other constraints. For example, one could constrain the absolute power reabsorbed rather than the fractional reabsorption. Furthermore, other forms of the approximate minimax problem statement can be generated introducing, for example, a suitably chosen cost function and performing an unconstrained minimization of the latter.

An advantage of the minimax method of antenna array excitation includes, among others, that the focal point can be adjusted to any point within the fatty layer to optimize reduction of fatty tissue within the constraints of the human physiological system without causing undue discomfort by excessively heating the skin or muscle layers. A disadvantage is that it is more complicated than the naive focus method, and may not result in as high efficiency.

Exemplary software code for implementing the minimax method of excitation is attached hereto as Exhibit A.

The combination of the bolus and the natural geometry of skin, fat, and muscle yields a physical structure resembling a parallel-plate waveguide where the metal top and bottom plates of the waveguide correspond to the skin and muscle, respectively, and the interior of the waveguide corresponds to the fat layer. Just as there could exist multiple propagating cylindrical modes in an ordinary parallel-plate waveguide, the approximate waveguide structure formed by the natural distribution of tissue also supports multiple propagating modes. Although coupling to the lowest-order mode to produce a converging cylindrical wave represents the fundamental mode of operation, multiple modes can also be used in combination. For example, the two lowest-order modes in combination could be used so as to cancel or partially cancel the field near the skin-fat interface to shift the focus of power density into the fat layer. A practical way to manipulate the excitation of multiple modes is to use the minimax optimization method.

Figure 14:
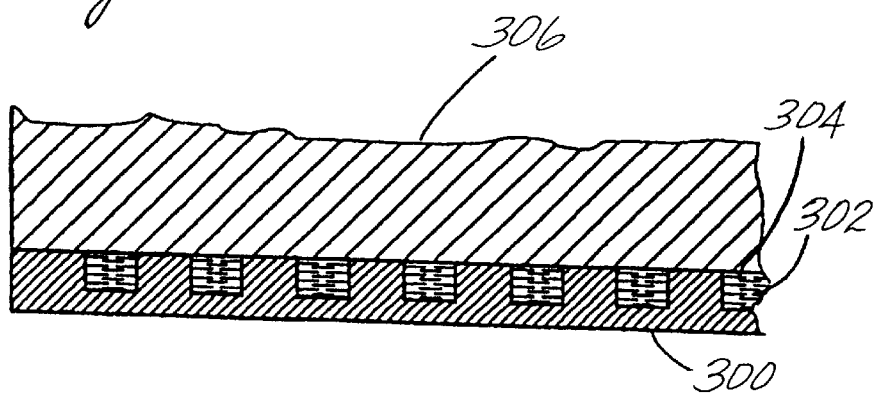
FIG. 14 is a cross-sectional side view of a bolus according to a presently preferred embodiment of the present invention.

Referring to FIG. 14, in a presently preferred embodiment of the present invention, the bolus actively cools the patient's skin, filters out unwanted and uncontrollable high spatial frequency components of the spectrum (generated, for example, by the fringing field at the edge of microstrip antennas), and provides optimal coupling of the antennas to the desired surface wave. The high dielectric layer 300 of the bolus is made of a water equivalent material such as an appropriately designed ceramic dielectric. Grooves 302 are machined into the ceramic, through which cooling water 304 is channeled. The channels are closed by bonding the high-dielectric grooved layer to the low-dielectric flat layer 306. Use of water equivalent material eliminates the dielectric contrast that would otherwise exist between the water in the cooling channels and the material forming the channels. By retaining the condition that their relative dielectric constants match, the condition that the conductivity of the water-equivalent material match that of water can be relaxed without introducing significant contrast.

Figure 15:
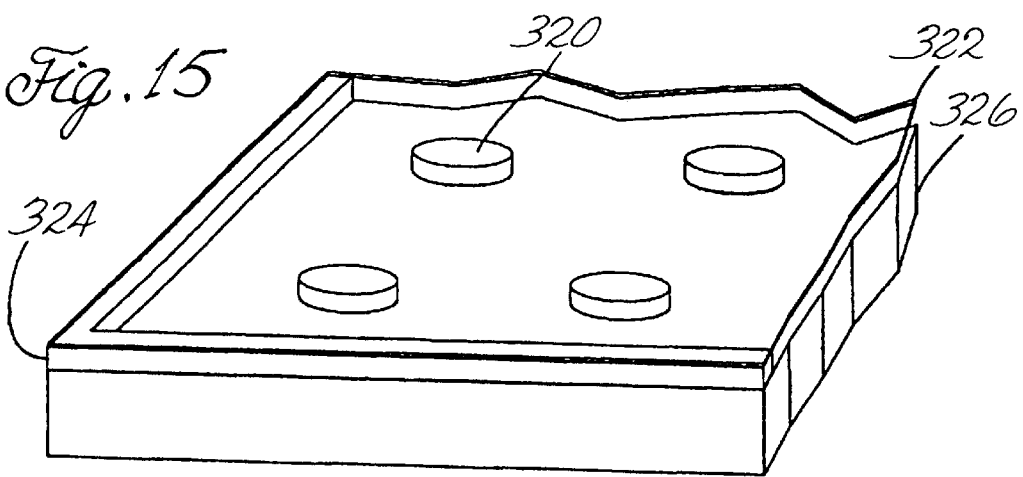
FIG. 15 is a perspective view, partly in cross section, of an alternate embodiment of the bolus according to the present invention.

Referring to FIG. 15, in an alternate embodiment of the bolus not requiring machined grooves, the body of the bolus is formed by using water-equivalent ceramic posts 320 supporting a very thin layer of plastic sheeting 322 stretched over the posts and bonded or clamped to an outer frame 324. The frame 324, which itself can be constructed of a water-equivalent material, and the posts 320 are preferably bonded to the low-dielectric layer 326. In either embodiment of the bolus, the choices of the value of the dielectric constant and the respective thicknesses of the high and low-dielectric constant layer of the bolus can be made by adjusting the aforementioned parameters of the bolus so that the improper pole (the pole located on the improper sheet of a two-sheeted Reimann surface corresponding to a so-called "leaky-wave pole") matches as closely as possible the complex intrinsic wavenumber of the fat layer. By doing this, there tends to be a field launched within the fat that is largely perpendicular to the tissue interfaces.

In an exemplary embodiment based on tissue parameters, a two-layer bolus designed using this principle has a low-dielectric constant layer with a relative dielectric constant of 6, and a thickness of 0.300 inches, while the thickness of the high-dielectric layer is 0.100 inch. Those skilled in the art will appreciate that the particular bolus described is one of many that could be designed using the disclosed principles. For example, the same principle may be used to design more complex boluses having three or more layers.

Figure 16:
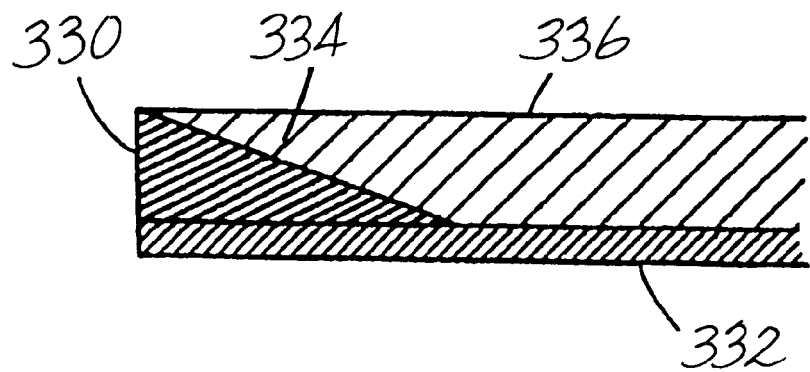
FIG. 16 is a cross-sectional side view of a wedge that can be used to augment the boluses of the present invention.

Referring to FIG. 16, the bolus assembly according to the present invention can be augmented with a lossy dielectric or ferrite wedge 330 as illustrated in the figure. The lossy wedge preferably, though not necessarily, sits upon the high-dielectric layer 332 and within a wedge-shaped groove 334 machined into the low-dielectric layer 336. This wedge encompasses in a frame-like manner the entire array at the array edge. The lossy wedge enables surface waves launched by the plurality of antennas within the array that are incident upon the edge of the array assembly to be absorbed, thereby preventing their reflection back into the tissue under the array assembly. The lossy wedge also helps prevent the formation of a local power-density hotspot that could potentially overheat tissue at the edge of the array.

The size of the aperture of the antenna array is dependent upon the operating frequency of the applicator for inducing lethal heating within the fatty layer. At below a certain frequency, the aperture size (physical footprint of the antenna aperture) is not large enough in terms of wavelengths to enable adequate focusing and hotspot reduction. It has also been found that the rate of tissue attenuation of the field increases with frequency. At above a certain frequency, the rate of attenuation is such that it is difficult to heat the fat because the field attenuates too much before it heats the fat. For any given depth of fat heating, therefore, an optimal frequency of operation exists between these extremes where the additional benefit of increasing aperture size in terms of wavelengths is canceled by the decrement in benefit caused by increasing tissue attenuation. This range of frequencies is roughly in the range of between 0.9 GHz and 9 GHz. A convenient frequency within this range is 2.45 GHz because this is currently assigned as an ISM band. However, for treating areas such as arms, thighs, and necks, where the fat pad and skin thickness may be less than that of the abdominal wall, and where the physical size of the aperture is more limited, an operation at a higher frequency in this range would be more appropriate.

In addition, the physical size of the bolus layers as well as the selection of dielectric constants of the bolus will be different for different frequencies within this frequency range and must be computed using the principles as disclosed. Generally, the higher the frequency of operation the thinner the bolus can be made. It will be understood to those skilled in the art that the physical size of the antennas may change (decrease in size with increasing frequency), as well as the size and number of shorting pins (in the monopole-like microstrip antennas) depending on the operating frequency.

One objective of the present invention is to effect the controlled reduction of fat-layer thickness within the body. The fat organ of the human body will respond to heat in a manner that depends on the volume heated and the level and duration which the tissue is heated. Manipulation of these parameters can be important for successful or optimal fat destruction and removal.

Fat cells can sustain lethal damage by sufficiently elevated temperature for a sufficient length of time. Conventional hyperthermia that has been applied to the treatment of tumors has sought a temperature within the tumor of typically 43° C. to 45° C. for a period of 30 to 60 minutes. However, it is known to those skilled in the art that for each 1° C. elevation in temperature within the target tissue, the treatment time can be roughly halved while maintaining the identical biological endpoint (for example cell necrosis). This is true for a number of different biological endpoints and for numerous tissue types. An elegant way of expressing this exponential time-temperature isoeffect relationship is through the Sapareto-Dewey integral which relates the actual tissue temperature T(t) in degrees C. as a function of time t to the equivalent amount of time $t_{43° C.eq}$ that would be required for the same isoeffect at the conventional hyperthermia temperature of 43° C. This integral is:

$$t_{43° C.eq} = \int_0^\tau R(T)(t))^{T(t)-43} dt, \quad (X)$$

where τ is the time period during which the thermal energy is induced and during which the tissue temperature subsequently decays to its baseline value, and R(T) is the base in the isoeffective relationship which is usually taken to be $$R(T) = \begin{cases} 2, T \geq 43° C. \\ 6, T < 43° C. \end{cases} \quad (XI)$$

Figure 17:
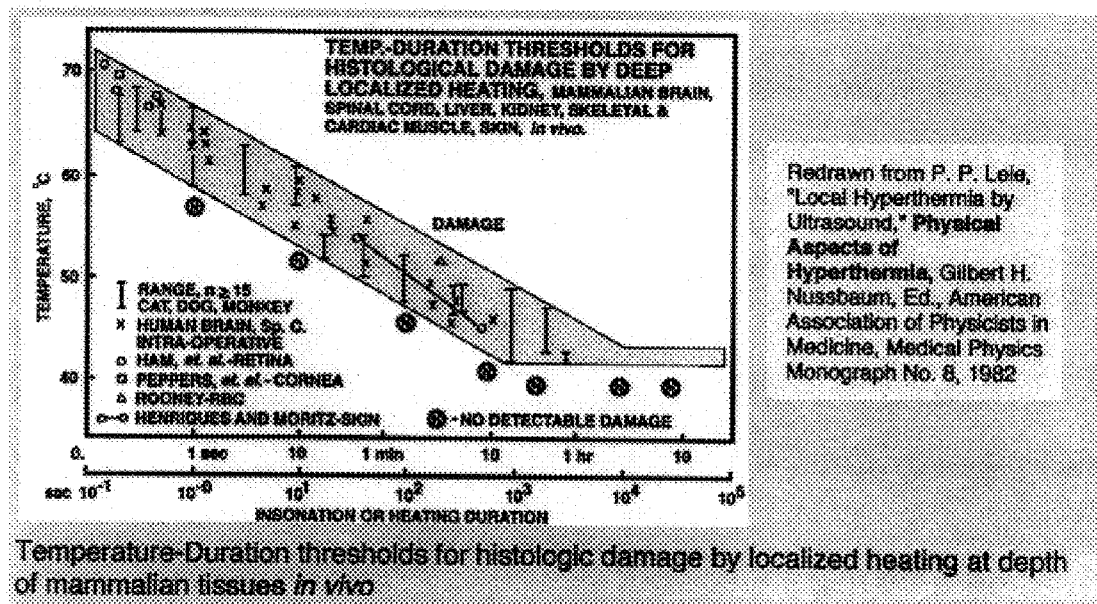
FIG. 17 is a diagram reproduced from the prior art illustrating the heat sensitivity of various tissues as a function of duration of heating.

For cases in which high peak temperatures are used, for example 60° C., the contribution to the integral from temperatures below 43° C. is essentially negligible. This exponential time-temperature relationship has been found to hold in its extreme even for heating durations as short as a second. Referring to FIG. 17, a figure is reproduced from P. P. Lele, "Local Hyperthermia by Ultrasound," P. P. Lele, "Local Hyperthermia by Ultrasound," Gilbert H. Nussbaum, Ed., Physical Aspects of Hyperthermia, American Association of Physicists in Medicine, Medical Physics Monograph No. 8, 1982, the contents of which are hereby incorporated by reference. In his article, Lele demonstrates a remarkable consistency in heat sensitivity of various tissues as a function of the duration of heating and shows that effective heat treatment as manifested by histological evidence of tissue damage can occur with very short-duration heating.

It has been discovered in accordance with the principles of the present invention that the applicator of the present invention can be operated in conjunction with Lele's findings and the Sapareto-Dewey integral to induce fatty cell damage through short duration, relatively high temperature pulses. There are several advantages to this method of treatment. By heating for short periods of time, the overall time for treatment can be reduced to a few seconds, thereby making practical the step of scanning the focus over the footprint of the device aperture to treat a large volume of tissue during a single session. In addition, by heating at a sufficiently fast rate, there is generally insufficient time for significant conductive cooling or cooling by circulating blood, thereby resulting in essentially adiabatic heating over the short heating time. Accordingly, this method allows prediction of the peak temperature induced in the tissue by the induced energy distribution and the heat capacity of the tissue, as opposed to the generally unknown level of blood perfusion.

It has further been discovered in accordance with the principles of the present invention that with the proper adjustment of heating time (of the order of a few seconds to a few tens of seconds) and induced energy density (that required to heat the fat to around 50° C. to 60° C.), one can obtain a lethal thermal dose within the fat while maintaining a small and non-injurious thermal dose within the muscle and skin. Because fat is more poorly perfused and has a much lower thermal conductivity than skin or muscle, the rate of heating can be adjusted so that it is relatively fast (i.e., heating duration is small compared to the thermal decay time) in the fat, and much slower (comparable to or larger than the thermal decay time) in the adjacent skin and muscle. Furthermore, because fat also has a lower heat capacity than skin or muscle, a given amount of energy density induced within the fat results in a temperature rise greater than that which results from an equal energy density induced in the skin and muscle. These factors enable effective application of heat according to the principles of the present invention in order to preferentially heat and fatty tissue.

Figure 18:
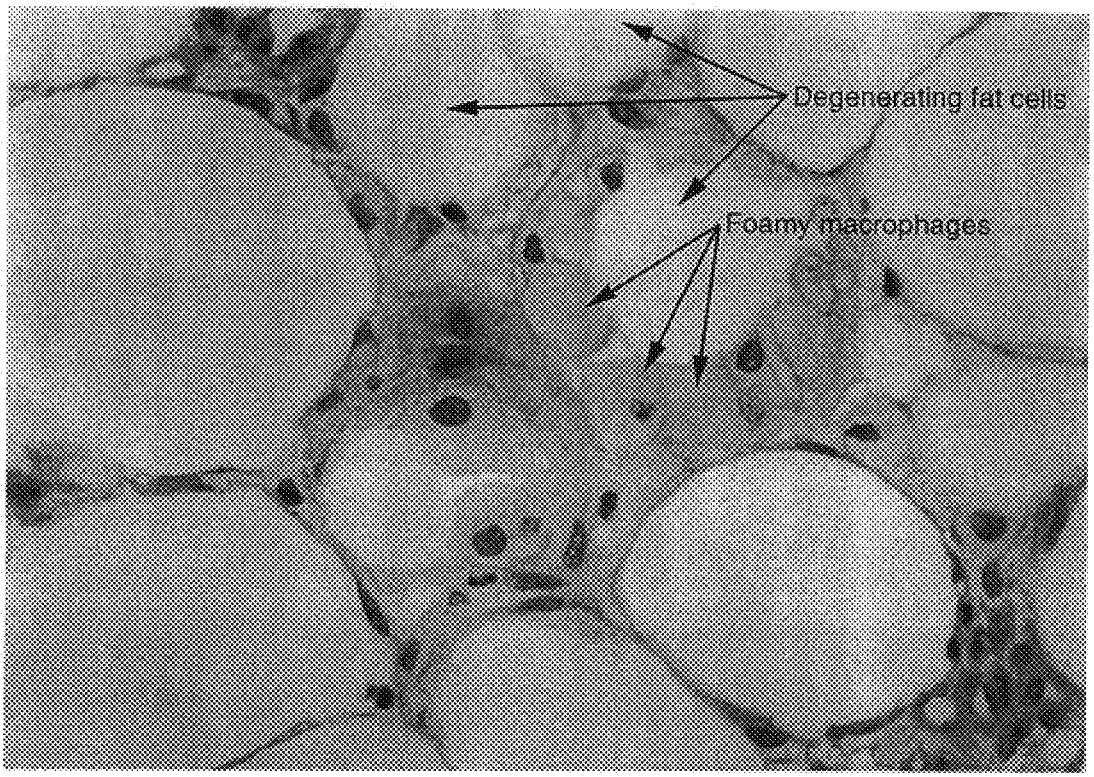
FIG. 18 is a photomicrograph of fat tissue excised from a human subject treated according to the principles of the present invention.

When the fat sustains a lethal level of thermal dose, the normal response of the human body is to mount an inflammatory reaction. If the inflammation is generally confined substantially within the fat layer, then the skin is uninjured and accordingly causes little or no discomfort. Shortly after the injury, it has been found that polymorphonuclear cells demarginate and infiltrate the injured fat. Cytokines are released that continue to amplify the inflammatory response which enters a chronic phase after a few days. During the chronic phase, lymphocytes and macrophages infiltrate the dead fat. The macrophages engulf the detritus of dead fat cells and lipid in a process called phagocytosis forming what are called foamy macrophages. The necrotic material is digested within the phagolysosomes of the macrophages and thereby removed from the body. FIG. 18 is a photomicrograph of fat tissue excised from a human volunteer treated in accordance with the principles of the present invention. The tissue was excised 20 days from the treatment during which the chronic phase of macrophage removal of fat was expected to be well under way. The figure shows dead fat cells surrounded by foamy macrophages consistent with the expected generic response to fat injury.

The generic process that occurs in many types of injured tissue and accounts, for example, for the complete disappearance of even large tumors after radiation or chemotherapy. It apparently occurs in fat due to local or systemic autoimmune attacks on the fat cells, in response to local trauma to fat, and in response to the injection of antibodies against fat-cell membranes that result in the killing of fat cells. When it involves a sufficient volume of fat, this process leads to a visible volumetric reduction in the fat volume at the site of fat injury. This volumetric reduction is termed lipoatrophy and has been reported in the literature to follow the destruction of fat cells by numerous mechanisms including those listed above. In contrast to autoimmune, traumatic, or injected-antibody injury to fat, the level and volume of tissue injury induced by the disclosed invention is controllable resulting in a controlled level of lipoatrophy which is cosmetically pleasing rather than disfiguring. Fibrosis is a consequence of tissue injury and tissue repair in the normal inflammatory response. It has not been reported as a prominent feature in most cases of lipoatrophy caused by disease or trauma, except for those associated with venous stasis. Nor has it been so extensive that it renders liposuction (an extreme form of fat trauma) disfiguring and inefficacious. However, to minimize the chance of cosmetically significant fibrosis, the volume and intensity of heating should be controlled so that, for example, large areas of confluent necrosis or hemorrhage in the fat is avoided. Multiple treatments to the same volume of fat spaced sufficiently separated in time to avoid thermotolerance (once or twice a week, for example) may be required for the timely removal of fat over the period of a few weeks to months.

In addition to fat removal by direct thermal killing, the applicator according to the present invention can be operated to reduce fat cells through a physiological mechanism known as apoptosis. Fat cells have been reported to undergo apoptosis when subjected to mild hyperthermic conditions (43° C. for 30 minutes). Apoptosis is a normal cellular process by which specific stimuli (such as heat, ionizing radiation, withholding of growth factors) cause the production of certain gene products that ultimately lead to the death of the cell. It has been termed "programmed cell death" and appears to be part of the normal turnover of many cell types within the body. It has been proposed as a physiological process by which fat cells are deleted from the body in states of starvation (in which growth factors are withheld thus inducing apoptosis). In vitro experiments reported in the literature suggest that 5% to 10% of the fat-cell population in a culture of fat cells exposed to mild hyperthermia will undergo apoptosis within nine days of heating. This is followed by macrophage removal of the dead fat cells.

Accordingly, the applicator according to the present invention can be used to induce lipoatrophy by at least two distinct methods. The first involves the well controlled noninvasive induction of lethal thermal damage to fat cells over defined volumes and with relatively short-duration periods of heating using the principle of the exponential time-temperature isoeffect relationship for tissue. The second involves the well controlled noninvasive induction of heat at levels to induce apoptosis within fat cells using either the principle of the exponential time-temperature isoeffect relationship for tissue, or using conventional hyperthermia.

To control the amount and distribution of thermal dose, the optimization methods for controlling the induced power densities can be amended as follows. One can compute the induced temperature as a function of time using such models as the bioheat equation or the effective-conductivity method based on assumed values of perfusion within the various tissues, skin, fat, and muscle. Accordingly, one can compute the thermal dose $t_{43°\ C.eq}^{(i)}$ at the $i^{th}$ sample point in a collection of sample points in which $r_i$ is set $\Omega'$, where the considerations for the selection of the spacing between the points in $\Omega'$ is similar to those used for set $\Omega$ as disclosed above. One can make the focal point of power induction the sample point j within $\Omega'$ and assign to it a power level of $P_j$ with a duration of $\tau_j$. Let the excitation voltage associated with this focal point be $V^{(j)}$. Finally, define a set $\Omega_{Target} \subset \Omega'$ containing all sample points within the target tissue that are to be treated and let its complement with respect to $\Omega'$ be $\overline{\Omega}_{Target}$.

Based on data summarized in Lele, for example, or carefully controlled thermal-dose escalation experiments, an acceptable thermal dose range (XII)

$$t_{43°Ceq}^{max} \geq t_{43°Ceq} \geq t_{43°Ceq}^{min} \tag{XII}$$

can be defined. Then one can solve the nonlinear-programming problem:

Minimize y with respect to $\{V^{(j)}, P_j, \tau_j\}$ subject to the constraints $$t_{43°Ceq}^{max} \geq t_{43°Ceq}^{(i)} \geq t_{43°Ceq}^{min}, \quad \text{for all } r_i \in \Omega_{Target}, \tag{XIII}$$

$$y \geq t_{43°Ceq}^{(i)}, \quad \text{for all } r_i \in \overline{\Omega}_{Target}.$$

The results of this optimization can then be analyzed when the perfusion levels deviate over an expected range to determine if significant over-treatment or under-treatment is occurring, and the nominal perfusion levels in the optimization can be modified as necessary.

It would be recognized by those skilled in the art that other types of optimization schemes using these principles set forth above can be formulated using, for example, an unconstrained integral performance index that seeks to penalize departures from a chosen thermal dose distribution within the target tissues. The system for choosing excitations from invasive or noninvasive heat-inducing sources of any kind can also be subjected to the same type of optimization coupled with the employment of the principles of short-duration, high-temperature hyperthermia as disclosed above. The disclosed optimization principles may be coupled with the use of the principles of short-duration, high-temperature hyperthermia to the treat other target tissues besides fat, such as tumors.

In addition, modifications to the system for determining the excitation of an array of heat-inducing applicators can be made without departing substantially from the principles disclosed herein. For example, one can use a transition zone representing a rim of tissue at the boundary of the target tissues where no thermal-dose sampling occurs to avoid burdening the optimization algorithm with minimizing thermal dose at points where little such minimization is possible. Additionally, one can add the sequencing of focal points as a degree of freedom available to the optimization algorithm to allow the algorithm to choose successive focal points so that overlapping non-target-tissue hotspots cause minimal thermal dose accumulation to the non-target tissues.

In yet another embodiment of the present invention, the fatty tissue may be infiltrated in order to enhance the effectiveness of the microwave applicator. Injection of the fatty tissue with saline and local anesthetics and epinephrine by transcutaneous injection has been used for tumescent liposuction surgery. Infiltration of the fatty layer either before or after treatment with a noninvasive heat delivery system may be used as an adjunct to the heat treatment to improve the cell kill or to modify the biological response in some way. For example, local injection of saline in a focal region of fat tends to increase the local microwave power absorption within the focal region. Infiltration with local anesthetic and epinephrine could sensitize the cells to heat and reduce the perfusion of the fat, both reducing the oxygenation of the fat cells making them more vulnerable to heat and reducing the convective cooling of the fat by blood allowing more efficient heating. Infiltration with other substances such as a soluble RGD (arginine-glycine-aspartate oligopeptide) analog may decrease the degree of fibrosis that results from tissue injury. Systemic delivery of heat sensitizers by an intravenous route, orally, or other routes could also improve the degree of fat-cell damage resulting from localized heating. The use of thermally sensitive liposomes encapsulating such sensitizers or biological response modifiers could be given intravenously for stimulated release locally within the fat to improve efficiency of cell-killing killing or modify the inflammatory and reparative process. It will be understood by those skilled in the art that other heat sensitizers and biological response modifiers are potential candidates for adjunctive use with the application of heat-mediated fat removal. Those skilled in the art would further appreciate that various alternations and modifications to the described invention could be made without departing from the scope of the present invention as set forth in the claims. Although the disclosed device and method of choosing the excitation is very general and allows for the scanning of foci or the production of multiple foci, one could nevertheless fix the excitation and use the device as a fixed-focus array. Alternatively, one could use a single element whose geometry and excitation mode generates a converging cylindrical wave of substantially vertical polarization (polarization perpendicular to the skin-fat interface) as a special case of the disclosed device. This special case is derived from the disclosed general case either by turning all but one antenna off, or by setting the number of antennas in the array to one. For example, although described with respect to fatty cell removal, the microwave applicator according to the present invention may be used for general therapeutic purposes involving hyperthermia.

What is claimed is:

1. A microwave applicator for inducing hyperthermia in target tissue comprising:

a plurality of antenna elements arranged in an array for launching a plurality of electromagnetic waves having a polarization adapted for generating a plurality of electromagnetic surface waves; and a control system, comprising a system for choosing antenna array excitations and a phase shifter, so that the control system adjusts amplitude and phase of the antenna array elements for converging the electromagnetic surface waves at the target tissue, thereby heating the target tissue.

2. The apparatus of claim 1 wherein the system for choosing antenna array excitations is implemented in software for a digital computer having an output coupled to the phase shifter.

3. The applicator of claim 1 wherein the system for choosing antenna array excitations further comprises:

means for holding input voltage to the antenna elements substantially constant; and means for adjusting phase to obtain constructive interference at a projected focus.

4. The applicator of claim 1 wherein the system for choosing antenna array excitations further comprises:

means for selecting a focal point;

means for fixing power level at the focal point; and means for reducing power level at points other than the focal point.

5. The apparatus of claim 1 wherein the phase shifter comprises a two-way power divider for channeling power in a single direction to multiple ports, and a compensating network for reducing the variation in insertion loss with phase shift.

6. The apparatus of claim 1 wherein the plurality of antenna elements include microstrip antennas comprising:

a ground plane;

a top patch insulated by a physical gap from the ground plane; a center pin connected to the top patch for feeding the antenna element;

a plurality of short circuiting pins placed symmetrically about the center pin for adjusting the resonant frequency and input impedance of the antenna element.

7. The apparatus of claim 1 further comprising an antenna protection circuit coupled to an antenna element, the antenna protection circuit comprising:

a PIN diode;

a PIN diode biasing circuit coupled to the PIN diode; and a detector, coupled to a PIN diode biasing circuit, for detecting power reabsorbed by the antenna element and comparing the detected power to a threshold, wherein the detector causes the PIN diode biasing circuit to bias the PIN diode as a function of the detected power such that the antenna element appears as a continuous and nonperturbing ground plane when the detected power exceeds the threshold.

8. The apparatus of claim 1 wherein the operating frequency of the applicator is in the range of frequencies of between about 0.9 GHz and about 9 GHz.

9. The apparatus of claim 8 wherein the operating frequency is approximately 2.45 GHz.

10. The apparatus of claim 1 further comprising a bolus structure coupled to the antenna elements, the bolus including:
   means for actively cooling skin during operation of the antenna array;
   means for filtering undesired spatial frequency components; and
   means for coupling the antenna elements to a desired surface wave.

11. The apparatus of claim 1 further comprising a bolus structure coupled to the antenna elements, the bolus including:
   a high dielectric layer made of a material having a dielectric constant substantially equivalent to water;
   a low dielectric layer adjacent the high dielectric layer;
   a plurality of grooves disposed substantially within the high dielectric layer for channeling fluid, wherein the high dielectric layer is bonded to the low dielectric layer to enclose the grooves.

12. The apparatus of claim 11 wherein the bolus structure further comprises a lossy wedge, connected to the low and high dielectric layers, for absorbing surface waves incident upon the edges of the antenna array.

13. The apparatus of claim 12 wherein the respective thicknesses and dielectric constants of the high and low dielectric layers are selected to substantially match leaky wave pole with the complex intrinsic wavenumber of fat layer.

14. The apparatus of claim 1 further comprising a bolus structure coupled to the antenna elements, the bolus including:
   a high dielectric layer;
   a low dielectric layer adjacent the high dielectric layer;
   a frame bonded to the low dielectric layer;
   a plurality of posts made of a material having a dielectric constant substantially equivalent to water; and
   a layer of plastic sheeting stretched over the posts and attached to the frame.

15. The apparatus of claim 13 wherein the bolus structure further comprises a lossy wedge, connected to the low and high dielectric layers, for absorbing surface waves incident upon the edges of the antenna array.

* * * * *